(12) United States Patent
Hinner et al.

(10) Patent No.: US 12,195,503 B2
(45) Date of Patent: *Jan. 14, 2025

(54) PROTEINS SPECIFIC FOR CD137

(71) Applicant: Pieris Pharmaceuticals GmbH, Freising-Weihenstephan (DE)

(72) Inventors: Marlon Hinner, Munich (DE); Christine Rothe, Dachau (DE); Shane Olwill, Freising (DE); Andrea Allersdorfer, Wolnzach (DE); Rachida Siham Bel Aiba, Munich (DE)

(73) Assignee: Pieris Pharmaceuticals GmbH, Freising-Weihenstephan (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/579,392

(22) Filed: Jan. 19, 2022

(65) Prior Publication Data

US 2022/0144901 A1    May 12, 2022

Related U.S. Application Data

(62) Division of application No. 15/571,611, filed as application No. PCT/EP2016/059959 on May 4, 2016, now Pat. No. 11,261,221.

(30) Foreign Application Priority Data

May 4, 2015  (EP) ..................... 15166184

(51) Int. Cl.
  *C07K 14/47*  (2006.01)
  *A61K 38/00*  (2006.01)
  *A61K 47/51*  (2017.01)

(52) U.S. Cl.
  CPC .............. *C07K 14/47* (2013.01); *A61K 47/51* (2017.08); *A61K 38/00* (2013.01); *C07K 2319/30* (2013.01)

(58) Field of Classification Search
  None
  See application file for complete search history.

(56) References Cited

U.S. PATENT DOCUMENTS

| | | | |
|---|---|---|---|
| 5,728,553 A | 3/1998 | Goodey et al. |
| 5,849,576 A | 12/1998 | Skerra et al. |
| 6,099,517 A | 8/2000 | Daugherty |
| 6,103,493 A | 8/2000 | Skerra et al. |
| 6,123,936 A | 9/2000 | Platz et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,620,413 B1 | 9/2003 | Desauvage et al. |
| 6,696,245 B2 | 2/2004 | Winter et al. |
| 7,250,297 B1 | 7/2007 | Beste et al. |
| 7,252,998 B2 | 8/2007 | Skerra et al. |
| 9,051,382 B2 | 6/2015 | Trentmann et al. |
| 9,260,492 B2 | 2/2016 | Matschiner et al. |
| 9,549,968 B2 | 1/2017 | Skerra et al. |
| 9,884,898 B2 | 2/2018 | Corvey et al. |
| 2003/0069395 A1 | 4/2003 | Sato et al. |
| 2005/0095244 A1 | 5/2005 | Jure-kunkel et al. |
| 2006/0088908 A1 | 4/2006 | Skerra et al. |
| 2013/0079286 A1 | 3/2013 | Skerra et al. |
| 2014/0288008 A1 | 9/2014 | Matschiner et al. |
| 2017/0114109 A1 | 4/2017 | Skerra et al. |
| 2017/0369542 A1 | 12/2017 | Trentmann et al. |
| 2018/0016312 A1 | 1/2018 | Bel Aiba et al. |
| 2018/0141988 A1 | 5/2018 | Hinner et al. |
| 2018/0148484 A1 | 5/2018 | Hinner et al. |

FOREIGN PATENT DOCUMENTS

| | | |
|---|---|---|
| DE | 4417598 A1 | 12/1995 |
| DE | 19641876 A1 | 4/1998 |
| DE | 19742706 A1 | 4/1999 |
| DE | 19926068 C1 | 1/2001 |
| EP | 0330451 A2 | 8/1989 |
| EP | 0361991 A2 | 4/1990 |
| JP | 2005503829 A | 2/2005 |

(Continued)

OTHER PUBLICATIONS

Zhang et al. ("Propagated perturbation from a peripheral mutation show interactions supporting WW domain thermostability" Structure; vol. 26, Issue 11, p. 1474-1484).*
Altschul et al., Gapped BLAST and PSI-BLAST: a new generation of protein database search programs, Nucleic Acids Res., 25(17):3389-3402 (1997).
Altschul, S. et al., Basic Local Alignment Search Tool; J. Mol. Biol., 215:403-410 (1990).
Amstutz, P. et al., In vitro display technologies: novel developments and applications, Curr. Opin. Biotechnol., 2001, 12:400-405.
Bachmann, Barbara J., Linkage Map of *Escherichia coli* K-12. Edition 8, Microbial. Rev., Jun. 1990, 54(2):130-197.
Beck, et al., Nucleotide Sequence and Genome Organisation of Filamentous Bacteriophages fl and fd, Gene, vol. 16, pp. 35-58, 1981.

(Continued)

*Primary Examiner* — Julie Ha
*Assistant Examiner* — Tara L Martinez
(74) *Attorney, Agent, or Firm* — Neal, Gerber & Eisenberg LLP

(57) ABSTRACT

The present disclosure provides human lipocalin muteins that bind CD137 and can be used in pharmaceutical applications, for example, as anti-cancer agents and/or immune modulators for the treatment or prevention of human diseases such as cancer, infectious diseases, and autoimmune diseases. The present disclosure also concerns methods of making CD137 binding lipocalin muteins described herein as well as compositions comprising such lipocalin muteins. The present disclosure further relates to nucleic acid molecules encoding such lipocalin muteins and to methods for generation of such lipocalin muteins and nucleic acid molecules. In addition, the application discloses therapeutic and/or diagnostic uses of these lipocalin muteins as well as compositions comprising one or more of such lipocalin muteins.

Figure 1:
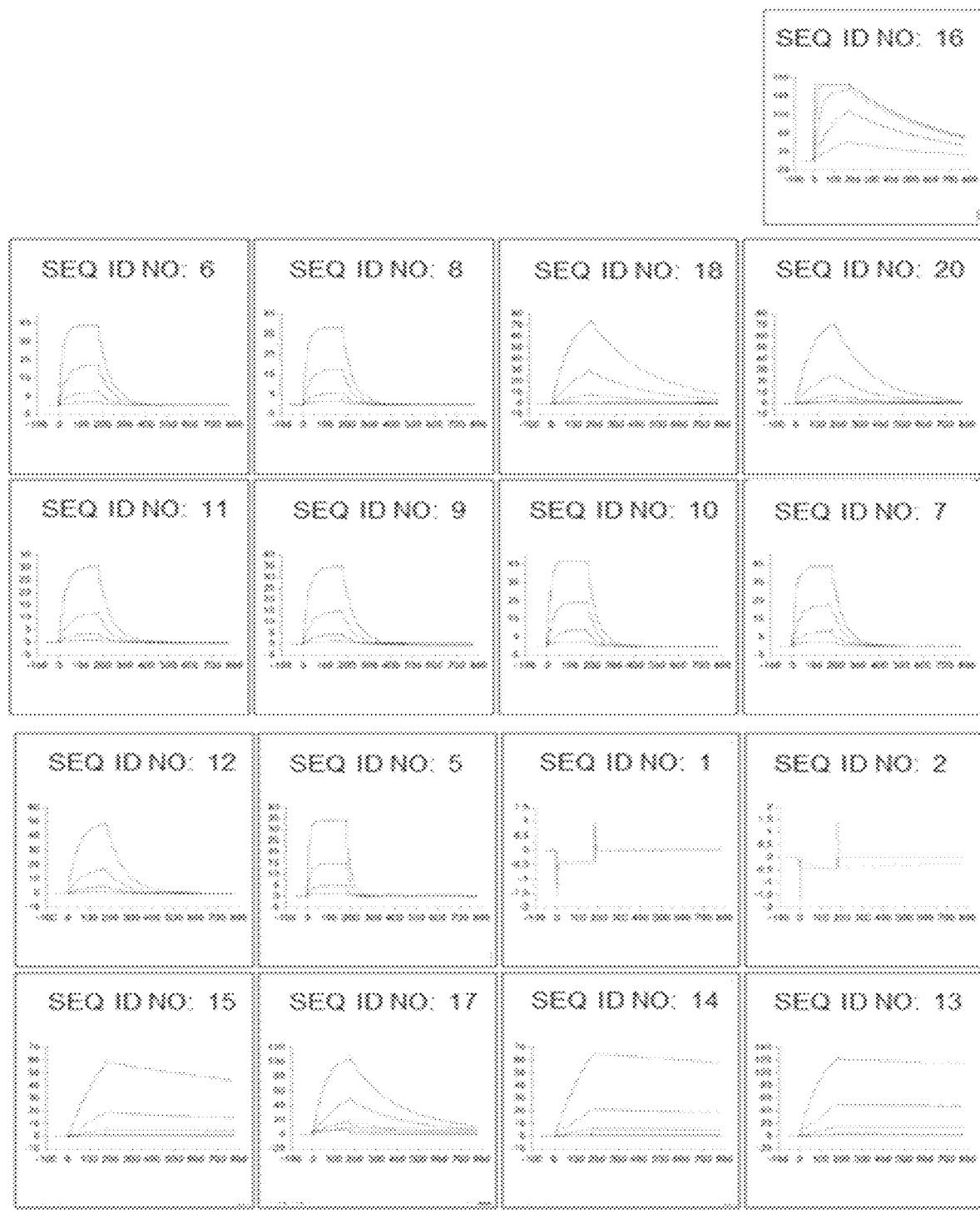

17 Claims, 5 Drawing Sheets
Specification includes a Sequence Listing.

(56) References Cited

FOREIGN PATENT DOCUMENTS

| | | |
|---|---|---|
| JP | 2007284351 A | 11/2007 |
| JP | 2018515085 A | 6/2018 |
| WO | 9623879 A1 | 8/1996 |
| WO | 9816873 A1 | 4/1998 |
| WO | 9916873 A1 | 4/1999 |
| WO | 9964016 A1 | 12/1999 |
| WO | 0075308 A1 | 12/2000 |
| WO | 03029462 A1 | 4/2003 |
| WO | 03029463 A2 | 4/2003 |
| WO | 03029471 A1 | 4/2003 |
| WO | 2005019254 A1 | 3/2005 |
| WO | 2005019255 A1 | 3/2005 |
| WO | 2005019256 A2 | 3/2005 |
| WO | 2006056464 A2 | 6/2006 |
| WO | 2007038619 A2 | 4/2007 |
| WO | 2008015239 A2 | 2/2008 |
| WO | 2009052390 A1 | 4/2009 |
| WO | 2009156456 A1 | 12/2009 |
| WO | 2015104406 A2 | 7/2015 |
| WO | 2016131804 A1 | 8/2016 |
| WO | 2016177762 A1 | 11/2016 |
| WO | 2016177802 A1 | 11/2016 |
| WO | 2018087108 A1 | 5/2018 |

OTHER PUBLICATIONS

Beste, G. et al., Small antibody-like proteins with prescribed ligand specificities derived from the lipocalin fold, Proc. Natl. Acad. Sci. USA, Mar. 1999, 96:1898-1903.
Bittker, J. et al., Nucleic acid evolution and minimization by nonhomologous random recombination, Nat. Biotechnol., Oct. 2002, 20:1024-1029.
Bos et al., OctoDEX.TM.—Controlled Release of Pharmaceutical Proteins from Hydrogels, Business Briefing: Pharmatech, 2003:1-6.
Breustedt, D. et al., Comparative ligand-binding analysis of ten human lipocalins, Biochim. Biophys. Acta, 2006, 1764:161-173.
Broders, O et al., Hyperphage. Improving antibody presentation in phage display, Methods Mol. Biol., 2003, 205:295-302.
Brody et al., Active and Passive Immunotherapy for Neurodegenerative Disorders, Annu. Rev. Neurosci., 2008, 31:175-193.
Bruckdorfer, T., et al., From Production of Peptides in Milligram Amounts for Research to Multi-Tons Quantities for Drugs of the Future, Curr. Pharm. Biotechnol., 2004, 5:29-43.
Bullock, W. et al., XL1-Blue: A High Efficiency Plasmid Transforming recA Escherichia coli Strain with Beta-Galactosidase Selection, Biotechniques, 1987, 5(4):376-378.
Bundgaard, J.R. et al., Molecular Cloning and Expression of a cDNA Encode NGAL: A Lipocalin Expressed in Human Neutrophils, Biochemical and Biophysical Research Communications, Aug. 15, 1994, pp. 1468-1475, vol. 202, No. 3, XP002036694.
Carnemolla et al., Phage Antibodies with PAN-Species Recognition of the Oncofoetal Angiogenesis Marker Fibronectin ED-B Domain, Int. J. Cancer, 1996, 68:397-405.
Chan et al., The primary structure of rat a 2μ globulin-related protein, Nucleic Acids Research, vol. 16, No. 23, pp. 11368, 1988.
"Chain A Crystal Structure of Siderocalin (Ngal, Lipocalin 2) Complexed With Trencam-3,2-Hopo, A Cepabactin Analogue," GenBank Accession No. 1X71_A, Sep. 24, 2008.
Coles, et al., The Solution Structure and Dynamics of Human Neutrophil Gelatinase-associated Lipocalin, J. Mol. Biol., vol. 289, pp. 139-157, 1999.
Dennis, M. et al., Albumin Binding as a General Strategy for Improving the Pharmacokinetics of Proteins, J. Biol. Chem., Sep. 20, 2002, 277(38):35035-35043.
Dodel et al., Immunotherapy for Alzheimer's disease, Lancet Neurology, Apr. 2003, 2:215-220.
Ebbinghaus et al., Diagnostic and Therapeutic Applications of Recombinant Antibodies: Targeting the Extra-Domain B of Fibronectin, A Marker of Tumor Angiogenesis, Curr. Pharm. Des., 2004, 10:1537-1549.
Fitzgerald, Kevin, In Vitro Display Technologies—New Tools for Drug Discovery, Reviews, vol. 5, No. 6, pp. 253-258, Jun. 2000.
Fling, S. and Gregerson, D., Peptide and Protein Molecular Weight Determination by Electrophoresis Using a High-Molarity Tris Buffer System without Urea, Anal. Biochem., 1986, 155:83-88.
Flower, Darren R., The lipocalin protein family: structure and function, Biochem. J., 1996, 318:1-14.
Frank, Ronald, The SPOT-synthesis technique Synthetic Peptide arrays on membrane supports—principles and applications, J. Immunol. Methods, 2002, 267:13-26.
Fuerteges, F. and Abuchowski, A., The Clinical Efficacy of Poly(Ethylene Glycol)-Modified Proteins,: J. Control. Release, 1990, 11:139-148.
Fujii, Phage display and beyond antibody—molecular target by antibody molecule, Seikagaku, 2010, vol. 82, No. 8, pp. 710-726, Abstract.
Gaillard, P. et al., Diphtheria toxin receptor-targeted brain drug delivery, International Congress Series., 2005, 1277:185-198.
Gaillard, P. et al., Targeted delivery across the blood-brain barrier, Expert Opin Drug Deliv., 2005, 2(2):299-309.
Gasteiger et al., ExPASy: the proteomics server for in-depth protein knowledge and analysis, Nucleic Acids Res., 2003, 31(13):3784-3788.
Gebauer, M. et al., Combinatorial Design of an Anticalin Directed against the Extra-Domain B for the Specific Targeting of Oncofetal Fibronectin, J. Mol. Biol., 425:780-802 (2013).
Goetz, D. et al., Ligand Preference Inferred from the Structure of Neutrophil Gelatinase Associated Lipocalin, Biochemistry, 2000, 39:1935-1941.
Gronwall et al., Selection and characterization of Affibody ligands binding to Alzheimer amyloid p peptides, J. Biotechnol., 2007, 128:162-183.
Haass et al., Soluble protein oligomers in neurodegeneration: lessons from the Alzheimer's amyloid (3-peptide, Nat. Rev. Mol. Cell. Biol., Feb. 2007, 8:101-112.
Hengen, Paul N., Methods and Reagents, Trends Biochem. Sci., vol. 21, pp. 75-76, 1996.
Hinner at al., "Costimulatory T cell engagement via novel bispecific anti-CD137/anti-HER2 protein based on Anticalin technology," poster, Sep. 18, 2015.
Hinner et al., "Costimulatory T cell engagement via a novel bispecific anti-CD137/anti HER2 protein," Journal for Immunotherapy of Cancer, vol. 3, 2015, p. 187.
Hoess, Ronald H., Phage Display of Peptides and Protein Domains, Structural Biology, vol. 3, pp. 572-279, 1993.
Hohlbaum et al., "Anticalins: the lipocalin family as a novel protein scaffold for the development of next-generation immunotherapies," Future Drugs Ltd, vol. 3, 2007, pp. 491-501.
Holzfeind, P. et al., Structural Organization of the Gene Encoding the Human Lipocalin Tear Prealbumin and Synthesis of the Recombinant Protein in Escherichia coli, Gene, vol. 139, pp. 177-183, 1994.
Hortschansky et al., The aggregation Kinetics of Alzheimer's (3-amyloid peptide is controlled by stochastic nucleation, Protein Sci., 2005, 14:1753-1759.
Hoyer, W. et al., Stabilization of a 13-hairpin in monomeric Alzheimer's amyloid-13 peptide inhibits amyloid formation, Proc. Natl. Acad. Sci. USA, Apr. 1, 2008, 105(13):5099-5104.
International Search Report for PCT/EP2017/078522, 5 pages (Feb. 5, 2018).
International Search Report and Written Opinion issued in corresponding application No. PCT/EP2016/059959 dated Jun. 29, 2016.
Karlsson et al., Kinetic analysis of monoclonal antibody-antigen interactions with a new biosensor based analytical system, J. Immunol. Methods, 1991, 145:229-240.
Kaspar et al., Fibronectin as target for tumor therapy, Int. J. Cancer, 2006, 118:1331-1339.
Khurana et al., Mechanism of thioflavin T binding to amyloid fibrils, J. Struct. Biol., 2005, 151:229-238.
Kim, H. et al., High-Affinity Recognition of Lanthanide(III) Chelate Complexes by a Reprogrammed Human Lipocalin 2, J. Am. Chem. Soc., 2009, 131:3565-3576.

(56) References Cited

OTHER PUBLICATIONS

Kjelsden, L. et al., Human Neutrophil Gelatinase-Associated Lipocalin and Homologous Proteins in Rat and Mouse, Biochimica et Biophysica Acta, vol. 1482, pp. 272-283, 2000.
Konig, T. and Skerra, A., Use of an albumin-binding domain for the selective immobilization of recombinant capture antibody fragments on ELISA plates, J. Immunol. Methods, 1998, 218:73-83.
Korean Office Action issued in corresponding application No. 10-2012-7017730 dated Jul. 28, 2018 with English translation.
Kraulis, et al., The Serum Albumin-Binding Domain of Streptococcal Protein G is a Three-Helical Bundle: A Heteronuclear NMR Study, FEBS Letters, vol. 378, pp. 190-194, 1996.
Leahy et al., Crystallization of a Fragment of Human Fibronectin: Introduction of Methionine by Site-Directed Mutagenesis to Allow Phasing via Selenomethionine, Proteins, 1994, 19:48-54.
Lichtlen et al., Antibody-based approaches in Alzheimer's research: safety, pharmacokinetics, metabolism, and analytical tools, J. Neurochem., 2007, 104:859-874.
Lohrengel, B. et al., Expression and Purification of Woodchuck Tumour Necrosis Factor Alpha, Cytokine, vol. 12, No. 6, pp. 573-577, Jun. 2000.
Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.
Lowman, H.B. Bacteriophage display and discovery of peptides leads for drug development, Annu. Rev. Biophys. Biomol. Struct., 1997, 26:401-424.
Lynch et al., "The promise of 4-1 BB (CD137)-mediated immunomodulation and the immunotherapy of cancer," Immunological Reviews, vol. 222, 2008, pp. 277-286.
Mateo, C. et al., Removal of Amphipathic Epitopes from Genetically Engineered Antibodies: Production of Modified Immunoglobulins with Reduced Immunogenicity, Hybridoma, 2000, 19(6):463-471.
Meidan et al., Emerging Technologies in Transdermal Therapeutics, Am. J. Ther., 2004, 11(4):312-316.
Moretto et al., Conformation-sensitive Antibodies against Alzheimer Amyloid-13 by Immunization with a Thioredoxin-constrained B-cell Epitope Peptide, J. Biol. Chem., 2007, 282(15):11436-11445.
Murakami, H. et al., Random insertion and deletion of arbitrary number of bases for codon-based random mutation of DNAs, Nat. Biotechnol., Jan. 2002, 20:76-81.
Notice of Reasons for Rejections dated Jan. 20, 2015 issued in Japanese Application No. 2012-542505, with English translation.
Osborn, B. et al., Pharmacokinetic and Pharmacodynamic Studies of a Human Serum Albumin-Interferon-a Fusion Protein in Cynomolgus Monkeys, J. Pharmacol. Exp. Ther., 2002, 303(2):540-548.
Paine et al., The Lipocalin website, Elsevier Science B.V., Biochimica et Biophysica Acta 1482, pp. 351-352, 2000.
Papiz, et al., The Structure of Beta-Lactoglobulin and Its Similarity to Plasma Retinol-Binding Protein, Nature, vol. 324, pp. 383-385, 1986.
Pervaiz, et al., Homology and Structure-Function Correlations Between a1-Acid Glycoprotein and Serum Retinol-Binding Protein and Its Relatives, 1987, The FASEB journal 1.3 (1987):209-214.
Pini et al., Design and Use of a Phage Display Library, J. Biol. Chem., Aug. 21, 1998, 273(34):21769-21776.
Pint, A. et al., Phage Display and Colony Filter Screening for High-Throughput Selection of Antibody Libraries, Comb. Chem. High Throughput Screen., 2002, 5:503-510.
Pujuguet et al., Expression of Fibronectin ED-A+ and ED-B+ Isoforms by Human and Experimental Colorectal Cancer, Am. J. Pathol., Feb. 1996, 148(2):579-592.
Redl, Bernhard, Human tear lipocalin, Biochim. Biophys. Acta, 2000, 1482:241-248.
Roberts, Richard W., Totally In Vitro Protein Selection Using mRNA-Protein Fusions and Ribosome Display, Current Opinion in Chemical Biology, vol. 3, pp. 268-273, 1999.
Rodi, D. and Makowski, L., Phage-display technology—finding a needle in a vast molecular haystack, Curr. Opin. Biotechnol., 1999, 10:87-93.
Schlehuber, S. and Skerra, A. et al., Duocalins, engineered ligand-binding proteins with dual specificity derived from the lipocalin fold, Biol. Chem., Sep. 2001, 382:1335-1342.
Schlehuber, S. et al., A Novel Type of Receptor Protein, Based on the Lipocalin Scaffold, with Specificity for Digoxigenin, J. Mol. Biol., 2000, 297:1105-1120.
Schlehuber S. et al., Lipocalins in drug discovery: from natural ligand-binding proteins to "anticalins", Drug Discov Today, 2005, vol. 10(1), pp. 23-33.
Schliemann et al., Antibody-based targeting of the tumor vasculature, Biochim. Biophys. Acta, 2007, 1776:175-192.
Schmidt et al., The Strep-tag system for one-step purification and high-affinity detection of capturing of proteins, Nat. Protoc., 2007, 2(6):1528-1535.
Schmidt, T. et al., Molecular Interaction Between the Strep-tag Affinity Peptide and its Cognate Target, Streptavidin, J. Mol. Biol., 1996, 255:753-766.
Schoepfer, Ralf, The pRSET Family of T7 Promoter Expression Vectors for *Escherichia coli*, Gene, vol. 124, pp. 83-85, 1993.
Schonfeld, D. et al. An engineered lipocalin specific for CTLA-4 reveals a combining site with structural and conformational features similar to antibodies, PNAS, 106(20): 8198-8203 (2009).
Skerra et al., 'Anticalins': a new class of engineered ligand-binding proteins with antibody-like properties, Reviews in Molecular Biotechnology, 2001, 74:257-275.
Skerra, A., et al., Lipocalins as a scaffold, Elsevier Science B.V., Biochimica et Biophysica Acta 1482, pp. 337-350, 2000.
Skerra, Anticalins as alternative binding proteins for therapeutic use; Current Opinion in Molecular Therapeutics, 9(4): 336-344 (Aug. 2007).
Skerra, Arne, Use of the tetracycline promoter for the tightly regulated production of a murine antibody fragment in *Escherichia coli*, Gene, 1994, 151:131-135.
Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.
Stoesz, S. et al., Overexpression of neu-related lipocalin (NRL) in neu-initiated but not ras or chemically initiated rat mammary carcinomas, Oncogene (1995), 11, pp. 2233-2241.
Studier, F.W., and Moffatt, B.A., Use of Bacteriophage T7 RNA Polymerase to Direct Selective High-level Expression of Cloned Genes, J. Mol. Biol., 1986, 189:113-130.
Tartof et al., Improved Media for Growing Plasmid and Cosmid Clones, Focus, Bethesda Research Laboratory, 1987, 9(2):12.
Tulasne, D. et al., C-Terminal Peptide of Thrombospondin-1 Includes Platelet Aggregation Through the Fc Receptor 'y-Chain-Associated Signaling Pathway and by Agglutination, Blood, vol. 98, No. 12, pp. 3346-3352, Dec. 1, 2001.
UniProt sequence G3SEI1 GORGO (<https://www.uniprot.org/uniprot/G3SEI1 integrated into UniProtKB Nov. 16, 2011).
Vajo, Z. and Duckworth, W., Genetically Engineered Insulin Analogs: Diabetes in the New Millennium, Pharmacol. Rev., 2000, 52(1):1-9.
Venturi, M. et al., High Level Production of Functional Antibody Fab Fragments in an Oxidizing Bacterial Cytoplasm, J. Mol. Biol., 2002, 315:1-8.
Virnekas et al., Trinucleotide phosphoramidites: ideal reagents for the synthesis of mixed oligonucleotides for random mutagenesis, Nucleic Acids Res, 1994, 22(25):5600-5607.
Vogt, M. and Skerra, A., Construction of an Artificial Receptor Protein ("Anticalin") Based on the Human Apolipoprotein D, ChemBioChem, 5: 191-199 (2004).
Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.
Wang et al., Expanding the Genetic Code of *Escherichia coli*, Science, Apr. 20, 2001, 292:498-500.

(56) References Cited

OTHER PUBLICATIONS

Wang et al., Expanding the genetic code, Chem. Comm., 2002, 1:1-11.
Wells, J. et al., Rapid Evolution of Peptide and Protein Binding Properties In Vitro, Current Opinion in Structural Biology, vol. 2, pp. 597-604, 1992.
Wilson, D. et al., The use of mRNA display to select high-affinity protein-binding peptides, Proc. Natl. Acad. Sci. USA, Mar. 27, 2001, 98(7):3750-3755.
Written Opinion for PCT/EP2017/078522, 6 pages (Feb. 5, 2018).
Yanisch-Perron, C. et al., Improved M13 phage cloning vectors and host strains: nucleotide sequences of the M13mp18 and pUC19 vectors, Gene, 1985, 33:103-119.
Zaccolo, M.et al., An Approach to Random Mutagenesis of DNA Using Mixtures of Triphosphate Derivatives of Nucleoside Analogues, J. Mal. Biol., 1996, 255:589-603.
Zardi, L. et al., Transformed human cells produce a new fibronectin isoform by preferential alternative splicing of a previously unobserved exon, EMBO J, 6(8):2337-42 (1987).

* cited by examiner

PROTEINS SPECIFIC FOR CD137

I. CROSS REFERENCE TO RELATED APPLICATIONS

This application is a divisional of U.S. patent application Ser. No. 15/571,611, filed Nov. 3, 2017 as a national stage entry of International Patent Application No. PCT/EP2016/059959, filed May 4, 2016, which claims priority to EP Patent Application No. 15166184.0 filed May 4, 2015, each of which is incorporated herein by reference in its entirety.

II. BACKGROUND

CD137 is a tumor-necrosis factor receptor (TNFR) superfamily molecule and whose activity may be involved in many immune-mediated autoimmune and inflammatory diseases. It is also a target for cancer immunotherapy.

CD137 signaling has been shown to be primordial for the maintenance and expansion of the immune response to antigens, as well as, for the generation of memory T-cells, Numerous studies of murine and human T cells indicate that CD137 promotes enhanced cellular proliferation, survival, and cytokine production (Croft, 2009, Nat Rev Immunol 9:271-285). Studies have indicated that some CD137 agonist mAbs increase costimulatory molecule expression and markedly enhance cytolytic T lymphocyte responses, resulting in anti-tumor efficacy in various models. CD137 agonist mAbs have demonstrated efficacy in prophylactic and therapeutic settings. Further, CD137 monotherapy and combination therapy tumor models have established durable antitumor protective T cell memory responses (Lynch, 2008, Immunol Rev. 22: 277-286), CD137 agonists also have been shown to inhibit autoimmune reactions in a variety of art-recognized autoimmunity models (Vinay, 2006, J Mol Med 84:726-736). This dual activity of CD137 offers the potential to provide anti-tumor activity while dampening autoimmune side effects that can be associated with immunotherapy approaches that break immune tolerance.

Consequently, based on the roles of CD137 in modulating immune response, there is a long-felt unmet need for compounds that bind human CD137, increase a CD137-mediated response, and thereby provide a potential therapeutic for treatment or prevention of various diseases and conditions, as cancer, infectious diseases, and autoimmune diseases.

Accordingly, it is an object of the present invention to provide such compounds, which are muteins derived from lipocalins. Muteins of various lipocalins are a rapidly expanding class of therapeutics and can be constructed through highly sophisticated artificial engineering to exhibit a high affinity and specificity against a target that is different than a natural ligand of wild-type lipocalins (see e.g., WO 99/16873, WO 00/75308, WO 03/029463, WO 03/029471 and WO 05/19256).

III. Definitions

The following list defines terms, phrases, and abbreviations used throughout the instant specification. All terms listed and defined herein are intended to encompass all grammatical forms.

As used herein, unless otherwise specified, "CD137" means human CD137. CD137 is also known as "4-1BB" or "tumor necrosis factor receptor superfamily member 9 (TNFRSF9)" or "induced by lymphocyte activation (ILA)". Human CD137 means a full-length protein defined by UniProt Q07011, a fragment thereof, or a variant thereof.

As used herein, "detectable affinity" means the ability to bind to a selected target with an affinity constant of generally at least about $10^{-5}$ M or below. Lower affinities are generally no longer measurable with common methods such as ELISA and therefore of secondary importance.

As used herein, "binding affinity" of a protein of the disclosure (e.g. a mutein of a lipocalin) or a fusion polypeptide thereof to a selected target (in the present case, CD137), can be measured (and thereby KD values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold. Said term also includes fragments of a mutein and variants as described herein. Lipocalin muteins of the present invention, fragments or variants thereof preferably retain the function of binding to CD37 as described herein.

The term "fragment" as used herein in connection with the muteins of the disclosure relates to proteins or peptides derived from full-length mature human tear lipocalin that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature lipocalin and are usually detectable in an immunoassay of the mature lipocalin. In general, the term "fragment", as used herein with respect to the corresponding protein ligand CD137 of a lipocalin mutein of the disclosure or of the combination according to the disclosure or of a fusion protein described herein, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature lipocalin can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild-type protein. Such an insertion or deletion may be introduced independently from each other in any of the peptide segments that can be subjected to mutagenesis in the disclosure. In one exemplary embodiment of the disclosure, an insertion of several mutations may be introduced into the loop AB of the chosen lipocalin scaffold (cf. International Patent Application WO 2005/019256 which is incorporated by reference its entirety herein).

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin mutein of the disclosure).

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild-type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a lipocalin (mutein) different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence".

The terms "reference sequence" and "wild-type sequence" are used interchangeably herein. A preferred wild-type lipocalin is shown in SEQ ID NO: 1 (Tlc) or SEQ ID NO: 2 (NGAL), respectively. Dependent on whether a lipocalin mutein of the present invention is based on Tlc or NGAL, respectively, the corresponding wild-type lipocalin may be used as reference sequence or wild-type sequence.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. The term "variant", as used herein with respect to the corresponding protein ligand CD137 of a lipocalin mutein of the disclosure or of the combination according to the disclosure or of a fusion protein described herein, relates to CD137 or fragment thereof, respectively, that has one or more such as 1, 2, 3, 4, 5, 6, 7, 8, 9, 10, 12, 14, 16, 18, 20, 22, 24, 26, 28, 30, 40, 50, 60, 70, 80 or more amino acid substitutions, deletions and/or insertions in comparison to a wild-type CD137 protein, respectively, such as a CD137 reference protein as deposited with SwissProt as described herein. A CD137 variant, respectively, has preferably an amino acid identity of at least 50%, 60%, 70%, 80%, 85%, 90% or 95% with a wild-type human CD137, such as a CD137 reference protein as deposited with SwissProt as described herein.

By a "native sequence" lipocalin is meant a lipocalin that has the same amino acid sequence as the corresponding polypeptide derived from nature. Thus, a native sequence lipocalin can have the amino acid sequence of the respective naturally-occurring lipocalin from any organism, in particular a mammal. Such native sequence polypeptide can be isolated from nature or can be produced by recombinant or synthetic means. The term "native sequence" polypeptide specifically encompasses naturally-occurring truncated or secreted forms of the lipocalin, naturally-occurring variant forms such as alternatively spliced forms and naturally-occurring allelic variants of the lipocalin. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide. As an illustrative example, the first 4 N-terminal amino acid residues (His-His-Leu-Leu) and the last 2 C-terminal amino acid residues (Ser-Asp) can be deleted in a tear lipocalin (Tlc) mutein of the disclosure without affecting the biological function of the protein, e.g. SEQ ID NOs: 5-11. In addition, as another illustrative example, certain amino acid residues can be deleted in a lipocalin 2 (NGAL) mutein of the disclosure without affecting the biological function of the protein, e.g. (Lys-Asp-Pro, positions 46-48) as to SEQ ID NO: 16.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sueqnece positions of one or more lipocalin muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild-type lipocalin 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a lipocalin mutein based on a reference scaffold in accordance with the disclosure, it is preferably to be understood that the positions of nucleotides/amino acids are structurally corresponding to the positions elsewhere in a (mutant or wild-type) lipocalin, even if they may differ in the indicated number, as appreciated by the skilled in light of the highly-conserved overall folding pattern among lipocalins.

The term "albumin" includes all mammal albumins such as human serum albumin or bovine serum albumin or rat serum albumin.

The term "organic molecule" or "small organic molecule" as used herein for the non-natural target denotes an organic molecule comprising at least two carbon atoms, but preferably not more than 7 or 12 rotatable carbon bonds, having a molecular weight in the range between 100 and 2000 Dalton, preferably between 100 and 1000 Dalton, and optionally including one or two metal atoms.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgous monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

IV. DESCRIPTIONS OF FIGURES

FIG. 1: provides typical measurements of on-rate and off-rate by surface plasmon resonance (SPR) for the interaction of various representative lipocalin muteins (SEQ ID NOs indicated in the graph) with human CD137 (Fc-fusion) as the target. The targets were immobilized via an anti-human IgG-Fc antibody, which was in turn immobilized on a sensor chip using standard amine coupling chemistry. The lipocalin muteins were employed as the soluble analyte which was flowed at different concentrations across the chip surface. There are clear SPR binding signals towards the human target, human CD137-Fc fusion protein (huCD137-Fc), for all muteins tested, while the negative controls of SEQ ID NO: 3 and SEQ ID NO: 4 exhibit no binding. The dissociation constants resulting from a fit (1:1 binding model) of the depicted data for all SEQ ID NOs are provided in Table 1.

Figure 2:
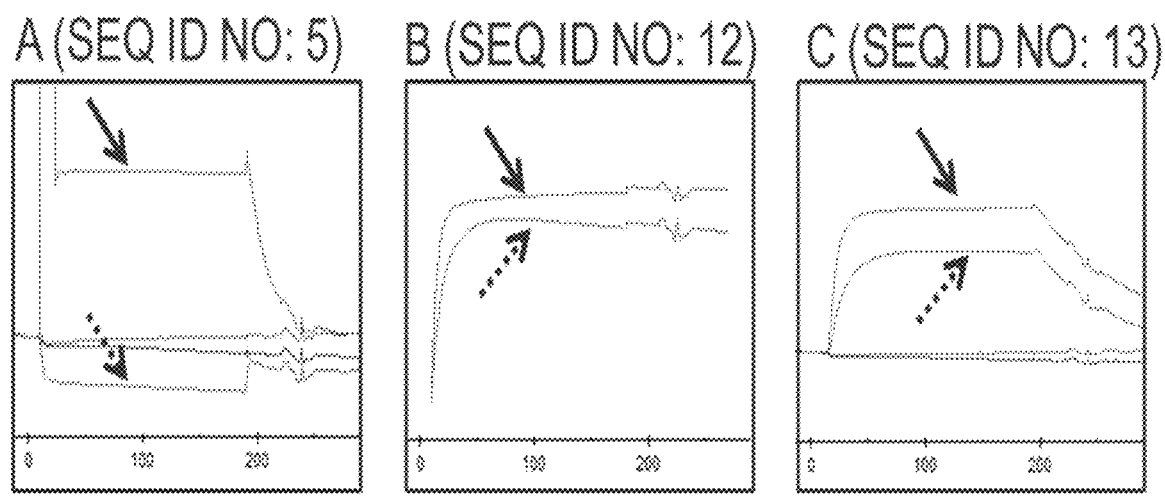

FIG. 2: provides representative examples of an SPR-based experiment designed to investigate whether muteins of SEQ ID NO: 5, SEQ ID NO: 12 and SEQ ID NO: 13 interfere with the binding of CD137 ligand (CD137L) to CD137. This is investigated by generating a complex of CD137 and CD137L on the SPR sensor chip, and checking whether the tested lipocalin muteins can bind to this complex or not. As a reference, CD137 in the absence of CD137L is incubated with the lipocalin muteins. In the figures, only the relevant segments of the sensorgrams are provided. The SPR trace for the binding of the respective lipocalin mutein to huCD137-Fc alone is marked with an arrow with a solid stem. The SPR trace for the binding of the respective lipocalin mutein to huCD137-Fc that has been saturated with CD137L is marked with an arrow with a broken stem. FIG. 2(A) shows SEQ ID NO: 5 can not bind to huCD137-Fc in the presence of CD137L. FIG. 2(B) and FIG. 2(C) show SEQ ID NO: 12 and SEQ ID NO: 13 bind to huCD137-Fc with a very similar response both in the absence and presence of CD137L, showing that there is no competition in the binding between the two lipocalin muteins and CD137L.

Figure 3:
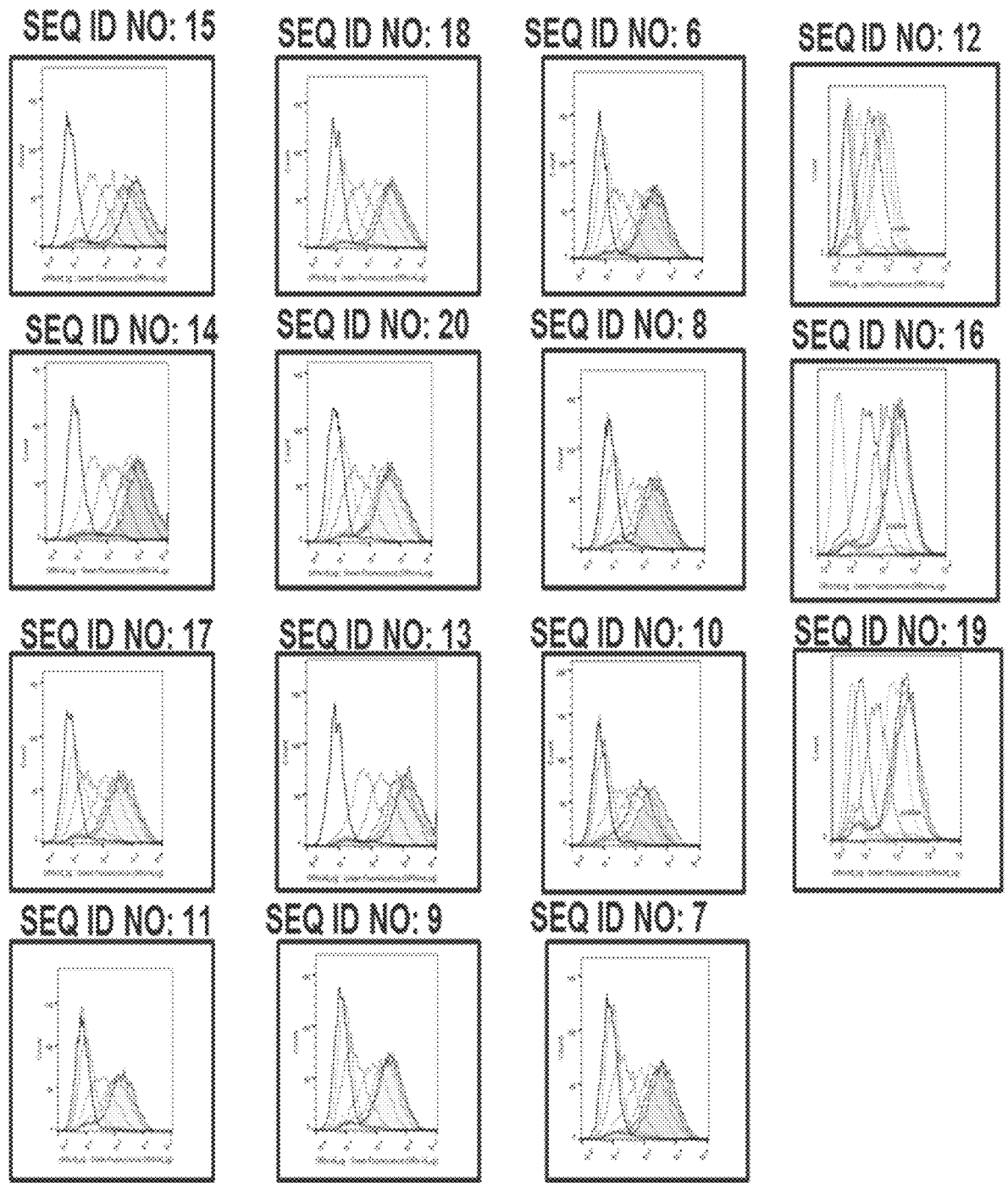

FIG. 3: shows representative examples of fluorescence-activated cell sorting (FACS) studies carried out in order to assess the specific binding of representative lipocalin muteins (SEQ ID NOs indicated in the graph) to human CD137 expressed on mammalian cells. Mock-transfected cells served as the negative control.

Figure 4:
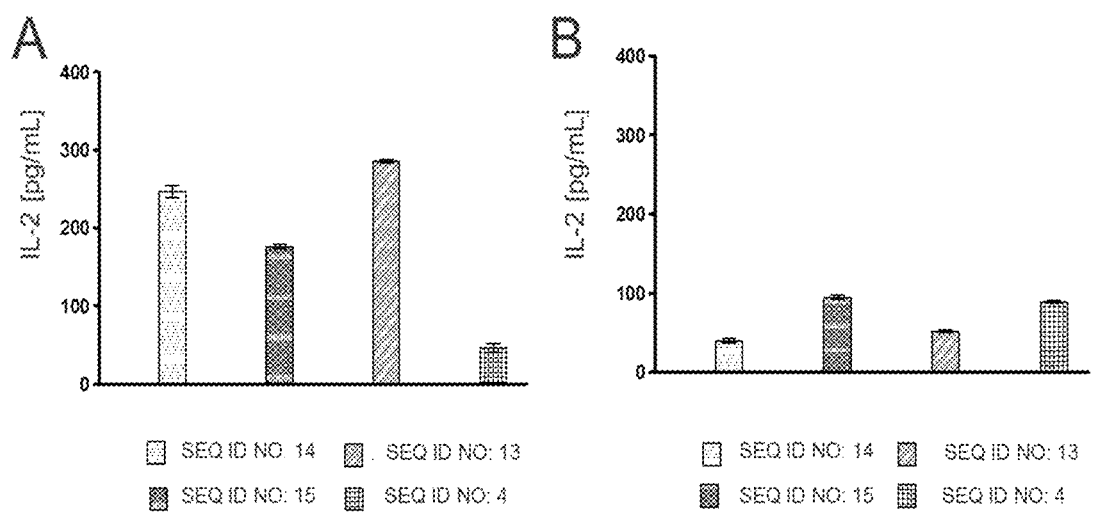

FIG. 4: depicts the results of a T-cell activation assay that was carried out in order to assess the ability of a set of representative CD137-binding lipocalin muteins (SEQ ID NO: 13, SEQ ID NO: 14 and SEQ ID NO: 15) to co-stimulate T-cell responses when coated on a plastic dish, by inducing clustering and concomitant downstream signaling of CD137 signaling. In addition, the activation of T-cells by incubation with soluble lipocalin muteins was tested to investigate whether the respective binders display agonistic activity in the absence of clustering. In FIG. 4(A) lipocalin muteins were coated onto a plastic dish together with an anti-human-CD3 antibody and purified T-cells were subsequently incubated on the coated surface in the presence of soluble anti-human CD28. In FIG. 4(B) an anti-human-CD3 antibody was coated onto a plastic dish and purified T-cells were subsequently incubated on the coated surface in the presence of soluble anti-human CD28 and the lipocalin muteins in solution. In both cases, supernatant interleukin 2 (IL-2) levels served as the readout. As a negative control SEQ ID NO: 4 was employed. In the experiment of FIG. 4(A), there is a clearly increased IL-2 concentration in the supernatant due to T-cell activation for the lipocalin muteins of SEQ ID NO: 13, SEQ ID NO: 14 and SEQ ID NO: 15 compared to the negative control of SEQ ID NO: 4. For the experiment utilizing the lipocalin muteins in solution in FIG. 4(B), there is no significant increase in IL-2 concentration in the supernatant for any of the lipocalin muteins tested compared to the negative control SEQ ID NO: 4. Taken together, FIGS. 4(A) and 4(B) show that the tested lipocalin muteins display the desired behavior: clustering CD137 on the T-cell surface via plastic-coated anti-CD137 muteins leads to the desired T-cell costimulation, while the respective mutein in solution—while binding to CD137 as shown in Example 4 and FIG. 3—does not induce any T-cell costimulation.

Figure 5:
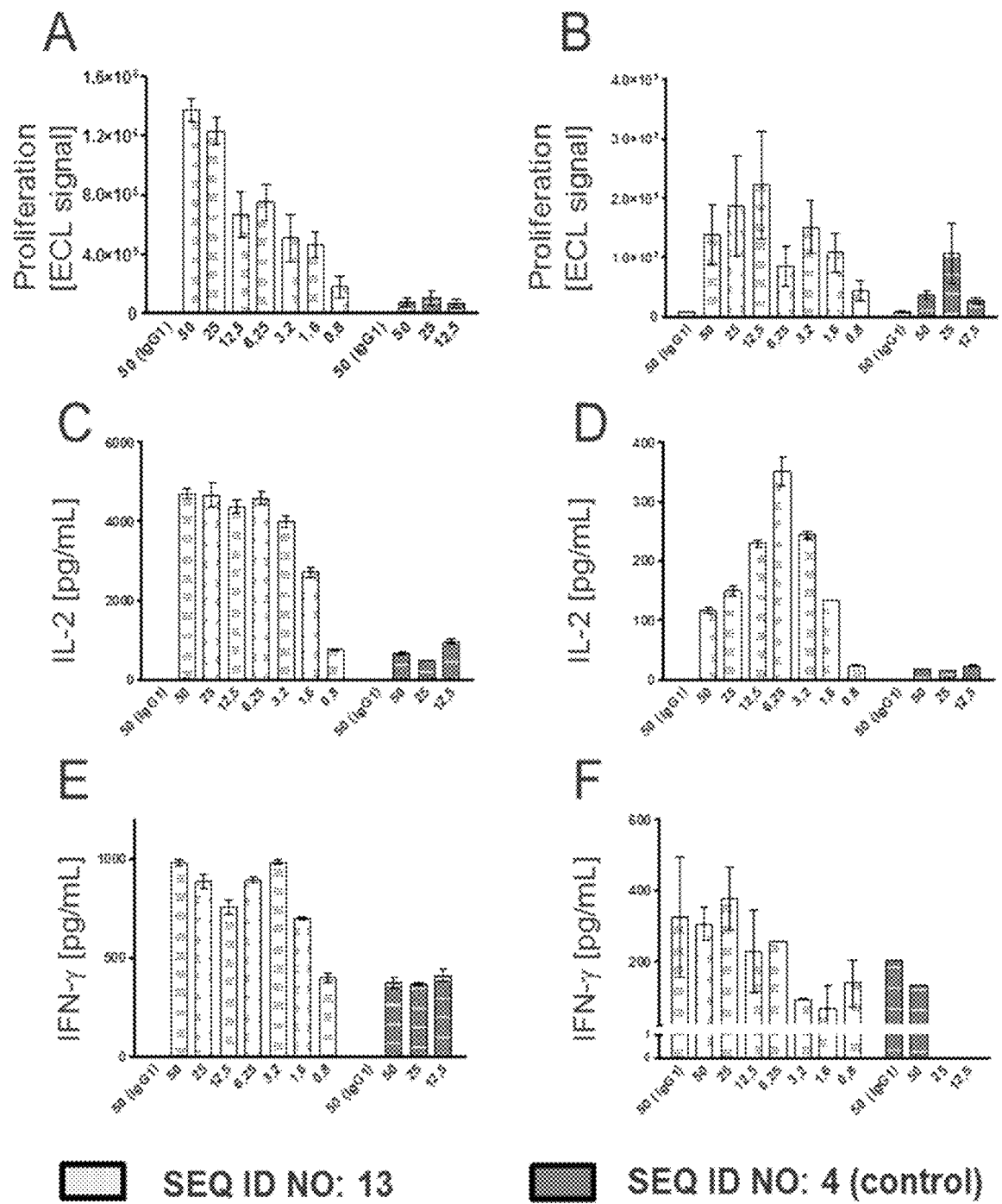

FIG. 5: provides the result of a T-cell activation experiment utilizing the CD137-binding lipocalin mutein of SEQ ID NO: 13 as the test molecule. SEQ ID NO: 4 was used as the negative control. The experiment was done utilizing additional, suboptimal anti-CD3 and anti-CD28 stimulation of T-cells with readouts in FIG. 5(A) continued proliferation of the T-cells after three days incubation using a 4 h BrdU pulse, FIG. 5(C) supernatant IL-2 concentration and FIG. 5(E) supernatant IFN-g levels. Alternatively, only suboptimal anti-CD3 concentration was utilized, with readouts in FIG. 5(B) continued proliferation, FIG. 5(D) supernatant IL-2 concentration and FIG. 5(F) supernatant IFN-g levels. The experiment demonstrates SEQ ID NO: 13-dose-dependent increases in proliferation, IL-2 and IFN-gamma levels both utilizing anti-CD3/anti-CD28 stimulation and anti-CD3 stimulation alone.

V. DETAILED DESCRIPTION OF THE DISCLOSURE

As used herein, a "lipocalin" is defined as a monomeric protein of approximately 18-20 kDA in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) *Biochim. Biophys. Acta* 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

As noted above, a lipocalin is a polypeptide defined by its supersecondary structure, namely cylindrical β-pleated sheet supersecondary structural region comprising eight β-strands connected pair-wise by four loops at one end to define thereby a binding pocket. The present disclosure is not limited to lipocalin muteins specifically disclosed herein. In this regard, the disclosure relates to a lipocalin mutein having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind CD137 with detectable affinity.

In one particular embodiment, a lipocalin mutein disclosed herein is a mutein of human tear lipocalin (TLPC or Tlc), also termed lipocalin-1, tear pre-albumin or von Ebner gland protein. The term "human tear lipocalin" or "Tlc" or "lipocalin-1" as used herein refers to the mature human tear lipocalin with the SWISS-PROT/UniProt Data Bank Accession Number P31025 (Isoform 1). The amino acid sequence shown in SWISS-PROT/UniProt Data Bank Accession Number P31025 may be used as a preferred "reference sequence", more preferably the amino acid sequence shown in SEQ ID NO: 1 is used as reference sequence.

In another particular embodiment, a lipocalin mutein disclosed herein is a mutein of human lipocalin 2. The term "human lipocalin 2" or "human Lcn 2" or "human NGAL" as used herein refers to the mature human neutrophil gelatinase-associated lipocalin (NGAL) with the SWISS-PROT/UniProt Data Bank Accession Number P80188. A human lipocalin 2 mutein of the disclosure may also be designated herein as "an hNGAL mutein". The amino acid sequence shown in SWISS-PROT/UniProt Data Bank Accession Number P80188 may be used as a preferred "reference sequence", more preferably the amino acid sequence shown in SEQ ID NO: 2 is used as reference sequence.

In some embodiments, a lipocalin mutein binding CD137 with detectable affinity may include at least one amino acid substitution of a native cysteine residue by another amino acid, for example, a serine residue. In some other embodiments, a lipocalin mutein binding CD137 with detectable affinity may include one or more non-native cysteine residues substituting one or more amino acids of a wild-type lipocalin. In a further particular embodiment, a lipocalin mutein according to the disclosure includes at least two amino acid substitutions of a native amino acid by a cysteine residue, hereby to form one or more cysteine briges. In some embodiments, said cysteine bridge may connect at least two loop regions. The definition of these regions is used herein in accordance with Flower (Flower, 1996, supra, Flower, et al., 2000, supra) and Breustedt et al. (2005, supra). In a related embodiment, the disclosure teaches one or more lipocalin muteins that are capable of activating downstream signaling pathways of CD137 by binding to CD137.

Proteins of the disclosure, which are directed against or specific for CD137, include any number of specific-binding protein muteins that are based on a defined protein scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50, with 1, 2, 3, 4, 5, 6, 7, 8, 9, 10, or 11 being preferred and 9, 10 or 11 being even more preferred. However, it is preferred that a lipocalin mutein of the disclosure is still capable of binding CD137.

In one aspect, the present disclosure includes various lipocalin muteins that bind CD137 with at least detectable affinity. In this sense, CD137 can be regarded a non-natural ligand of the reference wild-type lipocalin, where "non-natural ligand" refers to a compound that does not bind to wildtype lipocalins under physiological conditions. By engineering wildtype lipocalins with one or more mutations at certain sequence positions, the present inventors have demonstrated that high affinity and high specificity for the non-natural ligand, CD137, is possible. In some embodiments, at 1, 2, 3, 4, 5, 6, 7, 8, 9, 10, 11, 12 or even more nucleotide triplet(s) encoding certain sequence positions on wildtype lipocalins, a random mutagenesis may be carried out through substitution at these positions by a subset of nucleotide triplets.

Further, the lipocalin muteins of the disclosure may have a mutated amino acid residue at any one or more, including at least at any one, two, three, four, five, six, seven, eight, nine, ten, eleven or twelve, of the sequence positions corresponding to certain sequence positions of the linear polypeptide sequence of the reference lipocalin.

A protein of the disclosure may include the wild-type (natural) amino acid sequence of the "parental" protein scaffold (such as a lipocalin) outside the mutated amino acid sequence positions. In some embodiments, a lipocalin mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, NY). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human tear lipocalin as long as these deletions or insertion result in a stable folded/functional mutein (for example, Tlc muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature human tear lipocalin. As an illustrative example, the present disclosure also encompasses Tlc muteins as defined above, in which the first four N-terminal amino acid residues of the sequence of mature human tear lipocalin (His-His-Leu-Leu; positions 1-4) and/or the last two C-terminal amino acid residues (Ser-Asp; positions 157-158) of the linear polypeptide sequence of the mature human tear lipocalin have been deleted (SEQ ID NOs: 5-11). In addition, as another illustrative example, the present disclosure also encompasses NGAL muteins as defined above, in which amino acid residues (Lys-Asp-Pro, positions 46-48) of the linear polypeptide sequence of the mature human lipocalin 2 (hNGAL) have be deleted (SEQ ID NO: 16).

The amino acid sequence of a lipocalin mutein disclosed herein has a high sequence identity to the reference lipocalin when compared to sequence identities with other lipocalins. In this general context, the amino acid sequence of a lipocalin mutein of the disclosure is at least substantially similar to the amino acid sequence of the reference lipocalin, with the proviso that possibly there are gaps (as defined below) in an alignment that are the result of additions or deletions of amino acids. A respective sequence of a lipocalin mutein of the disclosure, being substantially similar to the sequences of the reference lipocalin, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of the reference lipocalin, with the proviso that the altered position or sequence is retained and that one or more gaps are possible.

As used herein, a lipocalin mutein of the disclosure "specifically binds" a target (for example, CD137) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In one embodiment, the lipocalin muteins of the disclosure are fused at its N-terminus and/or its C-terminus to a fusion partner which is a protein domain that extends the serum half-life of the mutein. In further particular embodiments, the protein domain is a Fc part of an immunoglobulin, a CH3 domain of an immunoglobulin, a CH4 domain of an immunoglobulin, an albumin binding peptide, or an albumin binding protein.

In another embodiment, the lipocalin muteins of the disclosure are conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immoglobulin, a CH4 domain of an immunoglobulin, an albumin binding peptide, and an albumin binding protein.

In yet another embodiment, the current disclosure relates to a nucleic acid molecule comprising a nucleotide sequence encoding a lipocalin mutein disclosed herein. The disclosure encompasses a host cell containing said nucleic acid molecule.

A. Lipocalin Muteins Specific for CD137

In one aspect, the present disclosure provides human lipocalin muteins that bind CD137 and useful applications therefor. The disclosure also provides methods of making CD137 binding proteins described herein as well as compositions comprising such proteins. CD137 binding proteins of the disclosure as well as compositions thereof may be used in methods of detecting CD137 in a sample or in methods of binding of CD137 in a subject. No such human lipocalin muteins having these features attendant to the uses provided by present disclosure have been previously described.

1. Exemplary Lipocalin Muteins Specific for CD137.

One embodiment of the current disclosure relates to a lipocalin mutein that is capable of binding CD137 with an affinity measured by a KD of about 300 nM, 100 nM, 75 nM, 50 nM, 25 nM, 10 nM or even lower such as 2 nM, for example, as determined by surface plasmon resonance (SPR) analysis essentially described in Example 4.

In another embodiment, the lipocalin mutein is capable of binding CD137 with an EC50 value of about 250 nM or lower, about 100 nM or lower, about 50 nM or lower, about 18 nM or lower, for example, as determined by a FACS analysis as essentially described in Example 6.

Another embodiment of the current disclosure provides a lipocalin mutein that is capable of activating downstream signaling pathways of CD137 by binding to CD137.

In some embodiments, compared to the negative control of SEQ ID NO: 4, a lipocalin mutein of the disclosure is capable of inducing higher IL-2 concentration, for example, when measured in a functional T-cell activation assay essentially described in Example 7.

In some other embodiments, compared to the negative control of SEQ ID NO: 4, a lipocalin mutein of the disclosure does not lead to higher IL-2 concentration, for example, when measured in a functional T-cell activation assay essentially described in Example 8.

In some embodiments, compared to the negative control of SEQ ID NO: 4, a lipocalin mutein of the disclosure is capable of inducing higher IL-2 and IFN-γ proliferation, for example, when measured in a functional T-cell activation assay essentially described in Example 9.

In one aspect, the present disclosure provides CD137-binding human tear lipocalin muteins.

In this regard, the disclosure provides one or more Tlc muteins that are capable of binding CD137 with an affinity measured by a KD of about 300 nM or lower and even about 100 nM or lower.

In some embodiments, such Tlc mutein comprises a mutated amino acid residue at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin (SEQ ID NO: 1).

In some particular embodiments, such Tlc mutein may contain a mutated amino acid residue at one or more positions corresponding to positions 26-34, 55-58, 60-61, 65, 104-106 and 108 of the linear polypeptide sequence of the mature human tear lipocalin.

In further particular embodiments, such Tlc mutein may further include a mutated amino acid residue at one or more positions corresponding to positions 101, 111, 114 and 153 of the linear polypeptide sequence of the mature human tear lipocalin.

In other particular embodiments, the Tlc may contain a mutated amino acid residue at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin.

In some further embodiments, the Tlc mutein may comprise at least 1, 2, 3, 4, 5, 6, 7, 8, 9, 10, 11, 12, 13, 14, 15, 16, 17, 18, 19, 20, 21, 22, 23, 24, 25, 26 or even more, mutated amino acid residues at one or more sequence positions corresponding to sequence positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin and wherein said polypeptide binds CD137, in particular human CD137.

In some still further embodiments, the disclosure relates to a polypeptide, wherein said polypeptide is a Tlc mutein, in comparison with the linear polypeptide sequence of the mature human tear lipocalin, comprising at least 1, 2, 3, 4, 5, 6, 7, 8, 9, 10, 11, 12 or even more, mutated amino acid residues at the sequence positions 526-34, 55-58, 60-61, 65, 104-106 and 108 and wherein said polypeptide binds CD137, in particular human CD137.

In some embodiments, a lipocalin mutein according to the disclosure may include at least one amino acid substitution of a native cysteine residue by e.g. a serine residue. In some embodiments, a Tlc mutein according to the disclosure includes an amino acid substitution of a native cysteine residue at positions 61 and/or 153 by another amino acid such as a serine residue. In this context it is noted that it has been found that removal of the structural disulfide bond (on the level of a respective nave nucleic acid library) of wild-type tear lipocalin that is formed by the cysteine residues 61 and 153 (cf. Breustedt, et al., 2005, supra) may provide tear lipocalin muteins that are not only stably folded but are also able to bind a given non-natural ligand with high affinity. In some particular embodiments, the Tlc mutein according to the disclosure includes the amino acid substitutions Cys 61→Ala, Phe, Lys, Arg, Thr, Asn, Gly, Gln, Asp, Asn, Leu, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein. However, tear lipocalin muteins that binds CD137 and that have the disulphide bridge formed between Cys 61 and Cys 153 are also part of the present disclosure.

In some embodiments, the elimination of the structural disulde bond may provide the further advantage of allowing for the (spontaneous) generation or deliberate introduction of non-natural artificial disulfide bonds into muteins of the disclosure, thereby increasing the stability of the muteins. For example, in some embodiments, either two or all three of the cysteine codons at position 61, 101 and 153 are replaced by a codon of another amino acid. Further, in some embodiments, a Tlc mutein according to the disclosure includes an amino acid substitution of a native cysteine residue at position 101 by a serine residue or a histidine residue.

In some embodiments, a mutein according to the disclosure includes an amino acid substitution of a native amino acid by a cysteine residue at positions 28 or 105 with respect to the amino acid sequence of mature human tear lipocalin.

Further, in some embodiments, a mutein according to the disclosure includes an amino acid substitution of a native arginine residue at positions 111 by a proline residue. Further, in some embodiments, a mutein according to the disclosure includes an amino acid substitution of a native lysine residue at positions 114 by a tryptophan residue or a glutamic acid.

In some embodiments, a CD137-binding Tlc mutein according to the disclosure includes, at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin (SEQ ID NO: 1), one or more of the following mutated amino acid residues: Ala 5→Val or Thr; Arg 26→Glu; Glu 27→Gly; Phe 28→Cys; Pro 29→Arg; Glu 30→Pro; Met 31→Trp; Leu 33→Ile; Glu 34→Phe; Thr 42→Ser; Gly 46→Asp; Lys 52→Glu; Leu 56→Ala; Ser 58→Asp; Arg 60→Pro; Cys 61→Ala; Lys 65→Arg or Asn; Thr 71→Ala; Val 85→Asp; Lys 94→Arg or Glu; Cys 101→Ser; Glu 104→Val; Leu 105→Cys; His 106→Asp; Lys 108→Ser; Arg 111→Pro; Lys 114→Trp; Lys 121→Glu; Ala 133→Thr; Arg 148→Ser; Ser 150→Ile and Cys 153→Ser. In some embodiments, a Tlc mutein according to the disclosure includes two or more, such as 3, 4, 5, 6, 7, 8, 9, 10, 11, 12, even more such as 13, 14, 15, 16, 17, 18, 19, 20, 21, 22, 23, 24, 25, 26 or all mutated amino acid residues at these sequence positions of the mature human tear lipocalin.

In some additional embodiments, the Tlc mutein binding CD137 includes one of the following sets of amino acid substitutions in comparison with the linear polypeptide sequence of the mature human tear lipocalin:

1. Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Cys 101→Ser; Glu 104→Val; Leu 105→Cys; His 106→Asp; Lys 108→Ser; Arg 111→Pro; Lys 114→Trp; Cys 153→Ser;
2. Ala 5→Thr; Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Arg; Val 85→Asp; Cys 101→Ser; Glu 104→Val; Leu 105→Cys; His 106→Asp; Lys 108→Ser; Arg 111→Pro; Lys 114→Trp; Lys 121→Glu; Ala 133→Thr; Cys 153→Ser; 157→Pro;
3. Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Asn; Lys 94→Arg; Cys 101→Ser; Glu 104→Val; Leu 105→Cys; His 106→Asp; Lys 108→Ser; Arg 111→Pro; Lys 114→Trp; Lys 121→Glu; Ala 133→Thr; Cys 153→Ser;
4. Ala 5→Val; Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Arg; Lys 94→Glu; Cys 101→Ser; Glu 104→Val; Leu 105→Cys; His 106→Asp; Lys 108→Ser; Arg 111→Pro; Lys 114→Trp; Lys 121→Glu; Ala 133→Thr; Cys 153→Ser; 157→Pro;
5. Arg 26→Glu; Glu 27→Gly; Phe 28→Cys; Pro 29→Arg; Glu 30→Pro; Met 31→Trp; Leu 33→Ile; Glu 34→Phe; Thr 42→Ser; Leu 56→Ala; Ser 58→Asp; Arg 60→Pro; Cys 61→Ala; Cys 101→Ser; Glu 104→Val; Leu 105→Cys; His 106→Asp; Lys 108→Ser; Arg 111→Pro; Lys 114→Trp; Ser 150→Ile; Cys 153→Ser; 157→Pro;
6. Arg 26→Glu; Glu 27→Gly; Phe 28→Cys; Pro 29→Arg; Glu 30→Pro; Met 31→Trp; Leu 33→Ile; Glu 34→Phe; Lys 52→Glu; Leu 56→Ala; Ser 58→Asp; Arg 60→Pro; Cys 61→Ala; Thr 71→Ala; Cys 101→Ser; Glu 104→Val; Leu 105→Cys; His 106→Asp; Lys 108→Ser; Arg 111→Pro; Lys 114→Trp; Ala 133→Thr; Arg 148→Ser; Ser 150→Ile; Cys 153→Ser; 157→Pro; or
7. Ala 5→Thr; Arg 26→Glu; Glu 27→Gly; Phe 28→Cys; Pro 29→Arg; Glu 30→Pro; Met 31→Trp; Leu 33→Ile; Glu 34→Phe; Gly 46→Asp; Leu 56→Ala; Ser 58→Asp; Arg 60→Pro; Cys 61→Ala; Thr 71→Ala; Cys 101→Ser; Glu 104→Val; Leu 105→Cys; His 106→Asp; Lys 108→Ser; Arg 111→Pro; Lys 114→Trp; Ser 150→Ile; Cys 153→Ser; 157→Pro.

In the residual region, i.e. the region differing from sequence positions 5, 26-31, 33-34, 42, 46, 52, 56, 58, 60-61, 65, 71, 85, 94, 101, 104-106, 108, 111, 114, 121, 133, 148, 150 and 153, a Tlc mutein of the disclosure may include the wild-type (natural) amino acid sequence outside the mutated amino acid sequence positions.

In still further embodiments, a Tlc mutein according to the current disclosure has at least 70% sequence identity or at least 70% sequence homology to the sequence of the mature human tear lipocalin (SEQ ID NO: 1). As an illustrative example, the mutein of the SEQ ID NO: 7 has an amino acid sequence identity or a sequence homology of approximately 81% with the amino acid sequence of the mature human tear lipocalin.

In further particular embodiments, a Tlc mutein of the disclosure comprises an amino acid sequence as set forth in any one of SEQ ID NOs: 5-11 or a fragment or variant thereof.

In further particular embodiments, a Tlc mutein of the disclosure has at least 75%, at least 80%, at least 85% or higher sequence identity to an amino acid sequence selected from the group consisting of SEQ ID NOs: 5-11.

The disclosure also includes structural homologues of a Tlc mutein having an amino acid sequence selected from the group consisting of SEQ ID NOs: 5-11, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said Tlc mutein.

A Tlc mutein according to the present disclosure can be obtained by means of mutagenesis of a naturally occurring form of human tear lipocalin. In some embodiments of the mutagenesis, a substitution (or replacement) is a conservative substitution. Nevertheless, any substitution—including non-conservative substitution or one or more from the exemplary substitutions below—is envisaged as long as the lipocalin mutein retains its capability to bind to CD137, and/or it has a sequence identity to the then substituted sequence in that it is at least 60%, such as at least 65%, at least 70%, at least 75%, at least 80%, at least 85% or higher sequence identity to the amino acid sequence of the mature human tear lipocalin (SWISS-PROT Data Bank Accession Number P31025).

In some additional embodiments, an hNGAL mutein of the disclosure is capable of interfering with the binding of CD137L to CD137, for example, as measured in a surface plasmon resonance (SPR) assay essentially described in Example 5.

In some particular embodiments, the present disclosure provides a lipocalin mutein that binds CD137 with an affinity measured by a $K_D$ of about 200 nM or lower, wherein the lipocalin mutein has at least 90% or higher, such as 95%, identity to the amino acid sequence of SEQ ID NO: 5.

In another aspect, the present disclosure relates to novel, specific-binding human lipocalin 2 (human Lcn2 or hNGAL) muteins directed against or specific for CD137.

In this regard, the disclosure provides one or more hNGAL muteins that are capable of binding CD137 with an affinity measured by a $K_D$ of 200 nM or lower, about 140 nM or lower, about 50 nM or lower, and even about 10 nM or lower. More preferably, the hNGAL muteins can have an affinity measured by a $K_D$ of about 5 nM or lower.

In some embodiments, an hNGAL mutein of the disclosure includes at one or more positions corresponding to positions 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SEQ ID NO: 2) a substitution.

In particular embodiments, a lipocalin mutein of the disclosure comprises at least 1, 2, 3, 4, 5, 6, 7, 8, 9, 10, 11, 12, 13, 14, 15, 16, 17, 18, 19, 20, 21, or even more, substitution(s) at a sequence position corresponding to sequence position 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SWISS-PROT Data Bank Accession Number P80188; SEQ ID NO: 2). Preferably, it is envisaged that the disclosure relates to a lipocalin mutein which comprises, in addition to one or more substitutions at positions corresponding to positions 36, 87 and/or 96 of the linear polypeptide sequence of the mature human NGAL, at one or more positions corresponding to positions 28, 40-41, 49, 52, 65, 68, 70, 72-73, 77, 79, 81, 83, 94, 100, 103, 106, 125, 127, 132 and 134 of the linear polypeptide sequence of the mature hNGAL a substitution.

In some still further embodiments, the disclosure relates to a polypeptide, wherein said polypeptide is an hNGAL mutein, in comparison with the linear polypeptide sequence of the mature hNGAL (SWISS-PROT Data Bank Accession Number P80188; SEQ ID NO: 2), comprising at least 1, 2, 3, 4, 5, 6, 7, 8, 9, 10, 11, 12, 13, 14, 15, 16, 17, 18, 19, 20, 21, or even more, mutated amino acid residues at the sequence positions 28, 36, 40-41, 49, 52, 65, 68, 70, 72-73, 77, 79, 81, 87, 96, 100, 103, 106, 125, 127, 132 and 134, and wherein said polypeptide binds CD137, in particular human CD137.

In some embodiments, a CD137-binding hNGAL mutein of the disclosure includes, at any one or more of the sequence positions 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SEQ ID NO: 2), one or more of the following mutated amino acid residues: Gln 28→His; Leu 36→Gln; Ala 40→Ile; Ile 41→Arg or Lys; Gln 49→Val, Ile, His, Ser or Asn; Tyr 52→Met; Asn 65→Asp; Ser 68→Met, Ala or Gly; Leu 70→Ala, Lys, Ser or Thr; Arg 72→Asp; Lys 73→Asp; Asp 77→Met, Arg, Thr or Asn; Trp 79→Ala or Asp; Arg 81→Met, Trp or Ser; Phe 83→Leu; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu and Lys 134→Tyr.

In some embodiments, an hNGAL mutein of the disclosure includes two or more, such as 3, 4, 5, 6, 7, 8, 9, 10, 11, 12, even more such as 13, 14, 15, 16, 17, 18, 19, 20, 21, 22, 23, 24 or all mutated amino acid residues at these sequence positions of the mature hNGAL.

In some additional embodiments, an hNGAL mutein of the disclosure, which binds to CD137 includes the following amino acid replacements in comparison with the linear polypeptide sequence of the mature hNGAL:

(a) Gln 28→His; Leu 36→Gln; Ala 40→Ile; Ile 41→Lys; Gln 49→Asn; Tyr 52→Met; Ser 68→Gly; Leu 70→Thr; Arg 72→Asp; Lys 73→Asp; Asp 77→Thr; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(b) Gln 28→His; Leu 36→Gln; Ala 40→Ile; Ile 41→Arg; Gln 49→Ile; Tyr 52→Met; Asn 65→Asp; Ser 68→Met; Leu 70→Lys; Arg 72→Asp; Lys 73→Asp; Asp 77→Met; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(c) Gln 28→His; Leu 36→Gln; Ala 40→Ile; Ile 41→Arg; Gln 49→Asn; Tyr 52→Met; Asn 65→Asp; Ser 68→Ala; Leu 70→Ala; Arg 72→Asp; Lys 73→Asp; Asp 77→Thr; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(d) Gln 28→His; Leu 36→Gln; Ala 40→Ile; Ile 41→Lys; Gln 49→Asn; Tyr 52→Met; Asn 65→Asp; Ser 68→Ala; Leu 70→Ala; Arg 72→Asp; Lys 73→Asp; Asp 77→Thr; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(e) Gln 28→His; Leu 36→Gln; Ala 40→Ile; Ile 41→Lys; Gln 49→Ser; Tyr 52→Met; Asn 65→Asp; Ser 68→Gly; Leu 70→Ser; Arg 72→Asp; Lys 73→Asp; Asp 77→Thr; Trp 79→Ala; Arg 81→Met; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(f) Gln 28→His; Leu 36→Gln; Ala 40→Ile; Ile 41→Lys; Gln 49→Val; Tyr 52→Met; Asn 65→Asp; Ser 68→Gly; Leu 70→Thr; Arg 72→Asp; Lys 73→Asp; Asp 77→Arg; Trp 79→Asp; Arg 81→Ser; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu; Lys 134→Tyr;

(g) Gln 28→His; Leu 36→Gln; Ala 40→Ile; Ile 41→Arg; Gln 49→His; Tyr 52→Met; Asn 65→Asp; Ser 68→Gly; Leu 70→Thr; Arg 72→Asp; Lys 73→Asp; Asp 77→Thr; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(h) Gln 28→His; Leu 36→Gln; Ala 40→Ile; Ile 41→Lys; Gln 49→Asn; Tyr 52→Met; Asn 65→Asp; Ser 68→Gly; Leu 70→Thr; Arg 72→Asp; Lys 73→Asp; Asp 77→Thr; Trp 79→Ala; Arg 81→Ser; Phe 83→Leu; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu; Lys 134→Tyr; or (i) Gln 28→His; Leu 36→Gln; Ala 40→Ile; Ile 41→Arg; Gln 49→Ser; Tyr 52→Met; Asn 65→Asp; Ser 68→Ala; Leu 70→Thr; Arg 72→Asp; Lys 73→Asp; Asp 77→Asn; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr.

In the residual region, i.e. the region differing from sequence positions 28, 36, 40-41, 49, 52, 65, 68, 70, 72-73, 77, 79, 81, 83, 87, 94, 96, 100, 103, 106, 125, 127, 132 and 134, an hNGAL mutein of the disclosure may include the wild-type (natural) amino acid sequence outside the mutated amino acid sequence positions.

In another embodiment, the hNGAL mutein has at least 70% or even higher sequence identity to the amino acid sequence of the mature human lipocalin 2 (SWISS-PROT Data Bank Accession Number P80188). As an illustrative example, the mutein of the SEQ ID NO: 17 has an amino acid sequence identity or a sequence homology of approximately 86.5% with the amino acid sequence of the mature hNGAL.

In further particular embodiments, a lipocalin mutein according to the current disclosure comprises an amino acid sequence selected from the group consisting of SEQ ID NOs: 12-20 or a fragment or variant thereof.

The amino acid sequence of a CD137-binding hNGAL mutein of the disclosure may have a high sequence identity, such as at least 70%, at least 75%, at least 80%, at least 82%, at least 85%, at least 87%, at least 90% identity, including at least 95% identity, to a sequence selected from the group consisting of SEQ ID NOs: 12-20.

The disclosure also includes structural homologues of an hNGAL mutein having an amino acid sequence selected from the group consisting of SEQ ID NOs: 12-20, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

An hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution—including non-conservative substitution or one or more from the exemplary substitutions below—is envisaged as long as the lipocalin mutein retains its capability to bind to CD137, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

In some additional embodiments, a Tlc mutein of the disclosure does not interfere with the binding of CD137L to CD137, for example, as measured in a surface plasmon resonance (SPR) assay essentially described in Example 5.

In some particular embodiments, the present disclosure provides a lipocalin mutein that binds CD137 with an affinity measured by a KD of about 5 nM or lower, wherein the lipocalin mutein has at least 90% or higher, such as 95%, identity to the amino acid sequence of SEQ ID NO: 13.

2. Applications of Lipocalin Muteins Specific for CD137

CD137 is a T-cell costimulatory receptor induced on T-cell receptor (TCR) activation (Nam et al., Curr. Cancer Drug Targets, 5:357-363 (2005); Watts et al., Annu. Rev. Immunol., 23:23-68 (2005)). In addition to its expression on activated CD4+ and CD8+ T cells, CD137 is also expressed on CD4+CD25+ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al., Annu. Rev. Immunol., 23:23-68 (2005)). On interaction with its ligand, CD137 leads to increased TCR-induced T-cell proliferation, cytokine production, functional maturation, and prolonged CD8+ T-cell survival (Nam et al., Curr. Cancer Drug Targets, 5:357-363 (2005), Watts et al., Annu. Rev. Immunol., 23:23-68 (2005)).

The CD137/CD137L interaction is involved in various aspects of an immune response. It appears to be important in inhibiting activation-induced cell death in T cells (Hurtado et al., J. Immunol. 158:2600, 1997), but abrogates anti-apoptotic effects of other cytokines in neutrophils (Heinisch et al., Eur. J. Immunol. 30:3441, 2001). CD137 thus may play a role in immune function homeostasis (Ebata et al., Eur. J. Immunol. 31:1210, 2001) and may represent a target costimulatory system that can be targeted in treatment of cancer or the inflammatory response (Blazer et al., J. Immunol. 166:174, 2001; Takahashi et al., Immunol. Lett. 76:183, 2001; Kim and Broxmeyer, J. Hematother. Stem Cell Res. 10:441, 2001; Kim et al., Cancer Res. 61:2031, 2001).

Numerous possible applications for the CD137-binding lipocalin muteins of the disclosure, therefore, exist in medicine. In one further aspect, the disclosure relates to the use of a CD137-binding lipocalin mutein disclosed herein for detecting CD137 in a sample as well as a respective method of diagnosis.

The present disclosure also involves the use of one or more CD137-binding lipocalin muteins as described for complex formation with CD137.

Therefore, in another aspect of the disclosure, the disclosed lipocalin muteins are used for the detection of CD137. Such use may include the steps of contacting one or more said muteins, under suitable conditions, with a sample suspected of containing CD137, thereby allowing formation of a complex between the muteins and CD137, and detecting the complex by a suitable signal.

The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The CD137-binding lipocalin muteins disclosed herein may also be used for the separation of CD137. Such use may include the steps of contacting one or more said muteins, under suitable conditions, with a sample supposed to contain CD137, thereby allowing formation of a complex between the muteins and CD137, and separating the complex from the sample.

In the use of the disclosed muteins for the detection of CD137 as well as the separation of CD137, the muteins and/or CD137 or a domain or fragment thereof may be immobilized on a suitable solid phase.

In still another aspect, the present disclosure features a diagnostic or analytical kit comprising a CD137-binding lipocalin mutein according to the disclosure.

In addition to their use in diagnostics, in yet another aspect, the disclosure contemplates a pharmaceutical composition comprising a mutein of the disclosure and a pharmaceutically acceptable excipient.

Furthermore, the present disclosure provides human lipocalin muteins that bind CD137 for use as anti-cancer agents and/or immune modulators. As such the lipocalin muteins of the present disclosure that bind CD137 are envisaged to be used in a method of treatment or prevention of human diseases such as cancer, infectious diseases, and autoimmune diseases. Accordingly, also provided are methods of treatment or prevention of human diseases such as cancer, infectious diseases, and autoimmune diseases in a subject in need thereof, comprising administering to said subject a therapeutically effective amount of a lipocalin mutein of the present invention that bind CD137.

In T cells CD137-mediated signaling leads to the recruitment of TRAF family members and activation of several kinases, including ASK-1, MKK, MAPK3/MAPK4, p38, and JNK/SAPK. Kinase activation is then followed by the activation and nuclear translocation of several transcription factors, including ATF-2, Jun, and NF-κB. In addition to augmenting suboptimal TCR-induced proliferation, CD137-mediated signaling protects T cells, and in particular, CD8+ T cells from activation-induced cell death (AICD).

The present disclosure encompasses the use of a CD137-binding lipocalin mutein of the disclosure or a composition comprising such lipocalin mutein for the binding of CD137, costimulating T-cells, and/or activating downstream signaling pathways of CD137 by binding to CD137, including enhancing IL-2 secretion and producing interferon IFN-γ.

The present disclosure also features a method of binding CD137 or costimulating T-cells, comprising applying one or more CD137-binding lipocalin muteins of the disclosure or of one or more compositions comprising such lipocalin muteins.

Furthermore, the present disclosure involves a method of activating downstream signaling pathways of CD137, including enhancing IL-2 secretion and producing interferon IFN-γ, comprising applying one or more CD137-binding lipocalin muteins of the disclosure or of one or more compositions comprising such lipocalin muteins.

The present disclosure also contemplates a method of inducing T lymphocyte proliferation, comprising applying one or more CD137-binding lipocalin muteins of the disclosure or of one or more compositions comprising such lipocalin muteins.

Moreover, absence of CD137/CD137L interactions prevents the development of certain autoimmune diseases (Seo et al., 2003, 2004). CD137/CD137L interactions are involved in the network of hematopoietic and nonhematopoietic cells in addition to the well characterized antigen-presenting cell-T cell interactions. Signaling through CD137L plays a critical role in the differentiation of myeloid cells and their cellular activities, suggesting that CD137L signals trigger and sustain inflammation. [Immune Network 2009;9(3):84-89].

The present disclosure encompasses the use of a CD137-binding lipocalin mutein of the disclosure that is capable of binding to CD137 competitively with CD137L or a composition comprising such lipocalin mutein for interference with binding of CD137L to CD137 and/or natural CD137L signaling.

The present disclosure also features a method of interfering with the binding of CD137L to CD137, comprising applying one or more CD137-competitive-binding lipocalin muteins of the disclosure or of one or more compositions comprising such lipocalin muteins.

Furthermore, the present disclosure involves a method of interfering with natural signaling of CD137L, comprising applying one or more CD137-competitive-binding lipocalin muteins of the disclosure or of one or more compositions comprising such lipocalin muteins.

The present disclosure also contemplates a method of reducing production of proinflammatory cytokines and chemokins, comprising applying one or more CD137-competitive-binding lipocalin muteins of the disclosure or of one or more compositions comprising such lipocalin muteins.

B. Lipocalin Mueteins of the Disclosure

Lipocalins are proteinaceous binding molecules that have naturally evolved to bind ligands. Lipocalins occur in many organisms, including vertebrates, insects, plants and bacteria. The members of the lipocalin protein family (Pervaiz, S., & Brew, K. (1987) FASEB J. 1, 209-214) are typically small, secreted proteins and have a single polypeptide chain. They are characterized by a range of different molecular-recognition properties: their ability to bind various, principally hydrophobic molecules (such as retinoids, fatty acids, cholesterols, prostaglandins, biliverdins, pheromones, tastants, and odorants), their binding to specific cell-surface receptors and their formation of macromolecular complexes. Although they have, in the past, been classified primarily as transport proteins, it is now clear that the lipocalins fulfill a variety of physiological functions. These include roles in retinol transport, olfaction, pheromone signalling, and the synthesis of prostaglandins. The lipocalins have also been implicated in the regulation of the immune response and the mediation of cell homoeostasis (reviewed, for example, in Flower, D. R. (1996) Biochem. J. 318, 1-14 and Flower, D. R. et al. (2000) Biochim. Biophys. Acta 1482, 9-24).

The lipocalins share unusually low levels of overall sequence conservation, often with sequence identities of less than 20%. In strong contrast, their overall folding pattern is highly conserved. The central part of the lipocalin structure consists of a single eight-stranded anti-parallel β-sheet closed back on itself to form a continuously hydrogen-bonded β-barrel. This β-barrel forms a central cavity. One end of the barrel is sterically blocked by the N-terminal peptide segment that runs across its bottom as well as three peptide loops connecting the β-strands. The other end of the β-barrel is open to the solvent and encompasses a target-binding site, which is formed by four flexible peptide loops. It is this diversity of the loops in the otherwise rigid lipocalin scaffold that gives rise to a variety of different binding modes each capable of accommodating targets of different size, shape, and chemical character (reviewed, e.g., in Flower, D. R. (1996), supra; Flower, D. R. et al. (2000), supra, or Skerra, A. (2000) Biochim. Biophys. Acta 1482, 337-350).

A lipocalin mutein according to the present disclosure may be a mutein of any chosen lipocalin. Examples of suitable lipocalins (also sometimes designated as "protein 'reference' scaffolds" or simply "scaffolds") of which a mutein may be used include, but are not limited to, tear lipocalin (lipocalin-1, von Ebner gland protein), retinol binding protein, neutrophil, lipocalin-type prostaglandin D-synthase, β-lactoglobulin, bilin-binding protein (BBP), apolipoprotein D (APO D), neutrophil gelatinase associated lipocalin (NGAL), tear lipocalin (Tlc), α2-microglobulin-related protein (A2m), 24p3/uterocalin (24p3), von Ebners gland protein 1 (VEGP 1), von Ebners gland protein 2 (VEGP 2), and Major allergen Can f1 precursor (ALL-1). In related embodiments, the lipocalin mutein is selected from the group consisting of human neutrophil gelatinase associated lipocalin (NGAL), human tear lipocalin (Tlc), human apolipoprotein D (APO D) and the bilin-binding protein of Pieris brassicae.

When used herein in the context of the lipocalin muteins of the present disclosure that bind to CD137, the term "specific for" includes that the lipocalin mutein is directed against, binds to, or reacts with CD137, respectively. Thus, being directed to, binding to or reacting with includes that the lipocalin mutein specifically binds to CD137, respectively. The term "specifically" in this context means that the lipocalin mutein reacts with a CD137 protein, as described herein, but essentially not with another protein. The term "another protein" includes any non-CD137 protein, respectively, including proteins closely related to or being homologous to CD137 against which the lipocalins disclosed herein are directed to. However, CD137 proteins, fragments and/or variants from species other than human such as those described in the context of the definition "subject" are not excluded by the term "another protein". The term "does not essentially bind" means that the lipocalin mutein of the present disclosure does not bind another protein, i.e., shows a cross-reactivity of less than 30%, preferably 20%, more preferably 10%, particularly preferably less than 9, 8, 7, 6 or 5%. Whether the lipocalin specifically reacts as defined herein above can easily be tested, inter alia, by comparing the reaction of a lipoclin mutein of the present disclosure with CD137 and the reaction of said lipocalin with (an) other protein(s). "Specific binding" can also be determined, for example, in accordance with Western blots, ELISA-, RIA-, ECL-, IRMA-tests, FACS, IHC and peptide scans.

The amino acid sequence of a lipocalin mutein according to the disclosure has a high sequence identity to respective lipocalin when compared to sequence identities with another lipocalin (see also above). In this general context the amino acid sequence of a lipocalin mutein of the combination according to the disclosure is at least substantially similar to the amino acid sequence of the corresponding lipocalin (the wild-type or reference lipocalin). A respective sequence of a lipocalin mutein of the combination according to the disclosure, being substantially similar to the sequences of the corresponding lipocalin, has in some to the wild-type (or reference) lipocalin, one or more amino acid embodiments at least 65%, at least 70%, at least 75%, at least 80%, at least 82%, at least 85%, at least 87%, at least 90% identity, including at least 95% identity to the sequence of the corresponding lipocalin. In this regard, a lipocalin mutein of the disclosure of course may contain, in comparison substitutions as described herein which renders the lipocalin mutein capable of binding to CD137, respectively. Typically a mutein of a lipocalin includes one or more mutations—relative to the native sequence lipocalin—of amino acids in the four loops at the open end of the ligand binding site of the lipocalin (cf. above). As explained above, these regions are essential in determining the binding specificity of a lipocalin mutein for a desired target. As an illustrative example, a mutein derived from a polypeptide of tear lipocalin, NGAL lipocalin or a homologue thereof, may have one, two, three, four or more mutated amino acid residues at any sequence position in the N-terminal region and/or in the three peptide loops BC, DE, and FG arranged at the end of the β-barrel structure that is located opposite to the natural lipocalin binding pocket. As a further illustrative example, a mutein derived from a polypeptide of tear lipocalin or a homologue thereof, may have no mutated amino acid residues in peptide loop DE arranged at the end of the β-barrel structure, compared to wild-type sequence of tear lipocalin.

A lipocalin mutein according to the disclosure includes one or more, such as two, three, four, five, six, seven, eight, nine, ten, eleven, twelve, thirteen, fourteen, fifteen, sixteen, seventeen, eighteen, nineteen or even twenty substitutions in comparison to the corresponding native lipocalin, provided that such a lipocalin mutein should be capable of binding to CD137, respectively. For example, a lipocalin mutein can have a substitution at a position corresponding to a distinct position (i.e. at a corresponding position) of the wild-type lipocalin having the wild-type sequence of, for example, tear lipocalin, NGAL lipocalin, or any other lipocalin disclosed herein. In some embodiments a lipocalin mutein of the combination according to the disclosure includes at least two amino acid substitutions, including 2, 3, 4, 5, ors even more, amino acid substitutions of a native amino acid by an arginine residue. Accordingly, the nucleic acid of a protein 'reference' scaffold as described herein is subject to mutagenesis with the aim of generating a lipocalin mutein which is capable of binding to CD137, respectively.

Also, a lipocalin mutein of the present disclosure can comprise a heterologous amino acid sequence at its N- or C-Terminus, preferably C-terminus, such as a SEQ ID NO: 23, e.g., Strep II tag without affecting the biological activity (binding to its target e.g. CD137, respectively) of the lipocalin mutein.

Likewise, a lipocalin mutein of the present disclosure may lack 1, 2, 3, 4 or more amino acids at its N-terminal end and/or 1, 2 or more amino acids at its C-terminal end, in comparison to the respective wild-type lipocalin; for example, SEQ ID NOs: 5-11 and 16.

Specifically, in order to determine whether an amino acid residue of the amino acid sequence of a lipocalin mutein different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild-type sequence" are used interchangeably herein.

In some embodiments a substitution (or replacement) is a conservative substitution. Nevertheless, any substitution—including non-conservative substitution or one or more from the exemplary substitutions listed below—is envisaged as long as the lipocalin mutein retains its capability to bind to CD137, respectively, and/or it has an identity to the then substituted sequence in that it is at least 60%, such as at least 65%, at least 70%, at least 75%, at least 80%, at least 85% or higher identical to the "original" sequence.

Conservative substitutions are generally the following substitutions, listed according to the amino acid to be mutated, each followed by one or more replacement(s) that can be taken to be conservative: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, Ile; Phe→Met, Leu, Tyr; Ser→Thr; Thr→Ser; Trp→Tyr; Tyr→Trp, Phe; Val→Ile, Leu. Other substitutions are also permissible and can be determined empirically or in accord with other known conservative or non-conservative substitutions. As a further orientation, the following eight groups each contain amino acids that can typically be taken to define conservative substitutions for one another:
  a. Alanine (Ala), Glycine (Gly);
  b. Aspartic acid (Asp), Glutamic acid (Glu);
  c. Asparagine (Asn), Glutamine (Gin);
  d. Arginine (Arg), Lysine (Lys);
  e. Isoleucine (Ile), Leucine (Leu), Methionine (Met), Valine (Val);
  f. Phenylalanine (Phe), Tyrosine (Tyr), Tryptophan (Trp);
  g. Serine (Ser), Threonine (Thr); and
  h. Cysteine (Cys), Methionine (Met)

If such substitutions result in a change in biological activity, then more substantial changes, such as the following, or as further described below in reference to amino acid classes, may be introduced and the products screened for a desired characteristic. Examples of such more substantial changes are: Ala→Leu, Ile; Arg→Gln; Asn→Asp, Lys, Arg, His; Asp→Asn; Cys→Ala; Gln→Glu; Glu→Gln; His→Lys; Ile→Met, Ala, Phe; Leu→Ala, Met, Norleucine; Lys→Asn; Met→Phe; Phe→Val, Ile, Ala; Trp→Phe; Tyr→Thr, Ser; Val→Met, Phe, Ala.

Substantial modifications in the biological properties of the lipocalin are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, methionine, alanine, valine, leucine, iso-leucine; (2) neutral hydrophilic: cysteine, serine, threonine; (3) acidic: asparitic acid, glutamic acid; (4) basic: asparagine, glutamine, histidine, lysine, arginine; (5) residues that influence chain orientation: glycine, proline; and (6) aromatic: tryptophan, tyrosine, phenylalanine.

Non-conservative substitutions will entail exchanging a member of one of these classes for another class. Any cysteine residue not involved in maintaining the proper conformation of the respective lipocalin also may be substituted, generally with serine, to improve the oxidative stability of the molecule and prevent aberrant crosslinking. Conversely, cysteine bond (s) may be added to the lipocalin to improve its stability.

Any mutation, including an insertion as discussed above, can be accomplished very easily on the nucleic acid, e.g. DNA level using established standard methods. Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) iso-leucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of tear lipocalin as long as these deletions or insertion result in a stable folded/functional mutein.

Modifications of the amino acid sequence include directed mutagenesis of single amino acid positions in order to simplify sub-cloning of the mutated lipocalin gene or its parts by incorporating cleavage sites for certain restriction enzymes. In addition, these mutations can also be incorporated to further improve the affinity of a lipocalin mutein for a given target such as CD137. Furthermore, mutations can be introduced in order to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation. It is also possible to deliberately mutate other amino acid sequence position to cysteine in order to introduce new reactive groups, for example for the conjugation to other compounds, such as polyethylene glycol (PEG), hydroxyethyl starch (HES), biotin, peptides or proteins, or for the formation of non-naturally occurring disulphide linkages. The generated thiol moiety may be used to PEGylate or HESylate the mutein, for example, in order to increase the serum half-life of a respective lipocalin mutein. Exemplary possibilities of such a mutation to introduce a cysteine residue into the amino acid sequence of a Tlc mutein include the substitutions Thr 40→Cys, Glu 73→Cys, Arg 90→Cys, Asp 95→Cys, and Glu 131→Cys. The generated thiol moiety at the side of any of the amino acid positions 40, 73, 90, 95 and/or 131 may be used to PEGylate or HESylate the mutein, for example, in order to increase the serum half-life of a respective Tlc mutein.

It is also possible to mutate other amino acid sequence positions to cysteine in order to introduce new reactive groups, for example, for the conjugation to other compounds, such as polyethylene glycol (PEG), hydroxyethyl starch (HES), biotin, peptides or proteins, or for the formation of non-naturally occurring disulphide linkages.

In some embodiments, if one of the above moieties is conjugated to a lipocalin mutein of the disclosure, conjugation to an amino acid side chain can be advantageous. Suitable amino acid side chains may occur naturally in the amino acid sequence of a human lipocalin or may be introduced by mutagenesis. In case a suitable binding site is introduced via mutagenesis, one possibility is the replacement of an amino acid at the appropriate position by a cysteine residue. For example, such mutation includes at least one of Thr 40→Cys, Glu 73→Cys, Arg 90→Cys, Asp 95→Cys or Glu 131→Cys substitution in the wild-type sequence of human tear lipocalin. The newly created cysteine residue at any of these positions can in the following be utilized to conjugate the mutein to moiety prolonging the serum half-life of the mutein, such as PEG or an activated derivative thereof.

With respect to a mutein of human Lipocalin 2, exemplary possibilities of such a mutation to introduce a cysteine residue into the amino acid sequence of a lipocalin including human Lipocalin 2 mutein to include the introduction of a cysteine (Cys) residue at at least at one of the sequence positions that correspond to sequence positions 14, 21, 60, 84, 88, 116, 141, 145, 143, 146 or 158 of the wild-type sequence of human NGAL. In some embodiments where a human Lipocalin 2 mutein of the disclosure has a sequence in which, in comparison to the sequence of the SWISS-PROT/UniProt Data Bank Accession Number P80188, a cysteine has been replaced by another amino acid residue, the corresponding cysteine may be reintroduced into the sequence. As an illustrative example, a cysteine residue at amino acid position 87 may be introduced in such a case by reverting to a cysteine as originally present in the sequence of SWISS-PROT accession No P80188. The generated thiol moiety at the side of any of the amino acid positions 14, 21, 60, 84, 88, 116, 141, 145, 143, 146 and/or 158 may be used to PEGylate or HESylate the mutein, for example, in order to increase the serum half-life of a respective human Lipocalin 2 mutein.

In another embodiment, in order to provide suitable amino acid side chains for conjugating one of the above compounds to a lipocalin mutein according to the present disclosure, artificial amino acids may be introduced by mutagenesis. Generally, such artificial amino acids are designed to be more reactive and thus to facilitate the conjugation to the desired compound. One example of such an artificial amino acid that may be introduced via an artificial tRNA is para-acetyl-phenylalanine.

For several applications of the muteins disclosed herein it may be advantageous to use them in the form of fusion proteins. In some embodiments, a lipocalin mutein of the disclosure is fused at its N-terminus or its C-terminus to a protein, a protein domain or a peptide, for instance, a signal sequence and/or an affinity tag.

Affinity tags such as the Strep-tag® or Strep-tag II (Schmidt, T. G. M. et al. (1996) *J. Mol. Biol.* 255, 753-766), the myc-tag, the FLAG-tag, the His$_6$-tag or the HA-tag or proteins such as glutathione-S-transferase also allow easy detection and/or purification of recombinant proteins are further examples of suitable fusion partners. Finally, proteins with chromogenic or fluorescent properties such as the green fluorescent protein (GFP) or the yellow fluorescent protein (YFP) are suitable fusion partners for lipocalin muteins of the disclosure as well.

In general, it is possible to label the lipocalin muteins of the disclosure with any appropriate chemical substance or enzyme, which directly or indirectly generates a detectable compound or signal in a chemical, physical, optical, or enzymatic reaction. An example for a physical reaction and at the same time optical reaction/marker is the emission of fluorescence upon irradiation or the emission of X-rays when using a radioactive label. Alkaline phosphatase, horseradish peroxidase and β-galactosidase are examples of enzyme labels (and at the same time optical labels) which catalyze the formation of chromogenic reaction products. In general, all labels commonly used for antibodies (except those exclusively used with the sugar moiety in the Fc part of immunoglobulins) can also be used for conjugation to the lipocalin muteins of the disclosure. The lipocalin muteins of the disclosure may also be conjugated with any suitable therapeutically active agent, e.g., for the targeted delivery of such agents to a given cell, tissue or organ or for the selective targeting of cells, e.g., of tumor cells without affecting the surrounding normal cells. Examples of such therapeutically active agents include radionuclides, toxins, small organic molecules, and therapeutic peptides (such as peptides acting as agonists/antagonists of a cell surface receptor or peptides competing for a protein binding site on a given cellular target). The lipocalin muteins of the disclosure may, however, also be conjugated with therapeutically active nucleic acids such as antisense nucleic acid molecules, small interfering RNAs, micro RNAs or ribozymes. Such conjugates can be produced by methods well known in the art.

As indicated above, a lipocalin mutein of the disclosure may in some embodiments be conjugated to a moiety that extends the serum half-life of the mutein (in this regard see also PCT publication WO 2006/56464 where such conjugation strategies are described with references to muteins of human neutrophile gelatinase-associated lipocalin with binding affinity for CTLA-4). The moiety that extends the serum half-life may be a polyalkylene glycol molecule, hydroxyethyl starch, fatty acid molecules, such as palmitic acid (Vajo & Duckworth 2000, *Pharmacol. Rev.* 52, 1-9), an Fc part of an immunoglobulin, a CH3 domain of an immunoglobulin, a CH4 domain of an immunoglobulin, an albumin binding peptide, or an albumin binding protein, transferrin to name only a few. The albumin binding protein may be a bacterial albumin binding protein, an antibody, an antibody fragment including domain antibodies (see U.S. Pat. No. 6,696,245, for example), or a lipocalin mutein with binding activity for albumin. Accordingly, suitable conjugation partners for extending the half-life of a lipocalin mutein of the disclosure include an albumin binding protein, for example, a bacterial albumin binding domain, such as the one of streptococcal protein G (Konig, T., & Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, His, Ile, Leu, or Lys; Xaa$_3$ is Ala, Asp, Phe, Trp, or Tyr; and Xaa$_4$ is Asp, Gly, Leu, Phe, Ser, or Thr as described in US patent application 2003/0069395 or Dennis et al. (Dennis, M. S., Zhang, M., Meng, Y. G., Kadkhodayan, M., Kirchhofer, D., Combs, D. & Damico, L. A. (2002) *J Biol Chem* 277, 35035-35043).

In other embodiments, albumin itself (Osborn, B. L. et al., 2002, *J. Pharmacol. Exp. Ther.* 303, 540-548), or a biological active fragment of albumin can be used as conjugation partner of a lipocalin mutein of the disclosure. The term "albumin" includes all mammal albumins such as human serum albumin or bovine serum albumin or rat albumine. The albumin or fragment thereof can be recombinantly produced as described in U.S. Pat. No. 5,728,553 or European patent applications EP 0 330 451 and EP 0 361 991. Recombinant human albumin (Recombumin®) Novozymes Delta Ltd. (Nottingham, UK) can be conjugated or fused to a lipocalin mutein of the disclosure in order to extend the half-life of the mutein.

If the albumin-binding protein is an antibody fragment it may be a domain antibody. Domain Antibodies (dAbs) are engineered to allow precise control over biophysical properties and in vivo half-life to create the optimal safety and efficacy product profile. Domain Antibodies are for example commercially available from Domantis Ltd. (Cambridge, UK and Mass., USA).

Using transferrin as a moiety to extend the serum half-life of the lipocalin muteins of the disclosure, the muteins can be genetically fused to the N or C terminus, or both, of non-glycosylated transferrin. Non-glycosylated transferrin has a half-life of 14-17 days, and a transferrin fusion protein will similarly have an extended half-life. The transferrin carrier also provides high bioavailability, biodistribution and circulating stability. This technology is commercially available from BioRexis (BioRexis Pharmaceutical Corporation, PA, USA). Recombinant human transferrin (DeltaFerrin™) for use as a protein stabilizer/half-life extension partner is also commercially available from Novozymes Delta Ltd. (Nottingham, UK).

If an Fc part of an immunoglobulin is used for the purpose to prolong the serum half-life of the lipocalin muteins of the disclosure, the SynFusion™ technology, commercially available from Syntonix Pharmaceuticals, Inc (Mass., USA), may be used. The use of this Fc-fusion technology allows the creation of longer-acting biopharmaceuticals and may for example consist of two copies of the mutein linked to the Fc region of an antibody to improve pharmacokinetics, solubility, and production efficiency.

Yet another alternative to prolong the half-life of the lipocalin muteins of the disclosure is to fuse to the N- or C-terminus of the muteins long, unstructured, flexible glycine-rich sequences (for example poly-glycine with about 20 to 80 consecutive glycine residues). This approach disclosed in WO2007/038619, for example, has also been term "rPEG" (recombinant PEG).

If polyalkylene glycol is used as conjugation partner, the polyalkylene glycol can be substituted, unsubstituted, linear or branched. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, such as polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. No. 6,500,930 or 6,620,413, carbohydrate oligo- and polymers such as starch or hydroxyethyl starch (HES) can be conjugated to a mutein of the disclosure for the purpose of serum half-life extension.

In addition, a lipocalin mutein disclosed herein may be fused to a moiety may confer new characteristics to the lipocalin muteins of the disclosure such as enzymatic activity or binding affinity for other molecules. Examples of suitable fusion partners are alkaline phosphatase, horseradish peroxidase, gluthation-S-transferase, the albumin-binding domain of protein G, protein A, antibody fragments, oligomerization domains or toxins.

In particular, it may be possible to fuse a lipocalin mutein disclosed herein with a separate enzyme active site such that both "components" of the resulting fusion protein together act on a given therapeutic target. The binding domain of the lipocalin mutein attaches to the disease-causing target, allowing the enzyme domain to abolish the biological function of the target.

The present disclosure also relates to nucleic acid molecules (DNA and RNA) that include nucleotide sequences encoding the lipocalin muteins of the disclosure. Since the degeneracy of the genetic code permits substitutions of certain codons by other codons specifying the same amino acid, the disclosure is not limited to a specific nucleic acid molecule encoding a lipocalin mutein as described herein but encompasses all nucleic acid molecules that include nucleotide sequences encoding a functional mutein. In this regard, the present disclosure provides nucleotide sequences encoding some lipocalin muteins of the disclosure as shown in SEQ ID NOs: 24-39.

In one embodiment of the disclosure, the method includes subjecting the nucleic acid molecule to mutagenesis at nucleotide triplets coding for at least one, or even more, of the sequence positions corresponding to the sequence positions 28, 36, 40-41, 49, 52, 65, 68, 70, 72-73, 77, 79, 81, 83, 87, 94, 96, 100, 103, 106, 125, 127, 132 and 134 of the linear polypeptide sequence of human NGAL (SEQ ID NO: 2).

In another embodiment of the method according to the disclosure, a nucleic acid molecule encoding a human tear lipocalin is firstly subjected to mutagenesis at one or more of the amino acid sequence positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of human tear lipocalin (SEQ ID NO: 1). Secondly, the nucleic acid molecule encoding a human tear lipocalin is also subjected to mutagenesis at one or more of the amino acid sequence positions 101, 111, 114 and 153 of the linear polypeptide sequence of the mature human tear lipocalin.

The disclosure also includes nucleic acid molecules encoding the lipocalin muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a lipocalin mutein as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a lipocalin mutein as described herein, and in particular a cloning vector containing the coding sequence of such a mutein can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion protein of the disclosure. Suitable host cells can be prokaryotic, such as *Escherichia coli* (*E. coli*) or *Bacillus subtilis*, or eukaryotic, such as *Saccharomyces cerevisiae*,

*Pichia pastoris*, SF9 or High5 insect cells, immortalized mammalian cell lines (e.g., HeLa cells or CHO cells) or primary mammalian cells.

The disclosure also relates to a method for the production of a lipocalin mutein as described herein, wherein the mutein, a fragment of the mutein or a fusion protein of the mutein and another polypeptide (e.g. another lipocalin mutein) is produced starting from the nucleic acid coding for the mutein by means of genetic engineering methods. The method can be carried out in vivo, the lipocalin mutein can for example be produced in a bacterial or eucaryotic host organism and then isolated from this host organism or its culture. It is also possible to produce a protein in vitro, for example by use of an in vitro translation system.

When producing the lipocalin mutein in vivo a nucleic acid encoding such mutein is introduced into a suitable bacterial or eukaryotic host organism by means of recombinant DNA technology (as already outlined above). For this purpose, the host cell is first transformed with a cloning vector that includes a nucleic acid molecule encoding a lipocalin mutein as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In some embodiments, a nucleic acid molecule, such as DNA, disclosed in this application may be "operably linked" to another nucleic acid molecule of the disclosure to allow expression of a fusion proteion of the disclosure. In this regard, an operable linkage is a linkage in which the sequence elements of the first nucleic acid molecule and the sequence elements of the second nucleic acid molecule are connected in a way that enables expression of the fusion protein as a single polypeptide.

In addition, in some embodiments, the naturally occurring disulfide bond between Cys 76 and Cys 175 may be removed in NGAL muteins of the disclosure. In some embodiments for Tlc muteins of the disclosure as well, the naturally occurring disulfide bond between Cys 61 and Cys 153 may be removed. Accordingly, such muteins can be produced in a cell compartment having a reducing redox milieu, for example, in the cytoplasma of Gram-negative bacteria.

In case a lipocalin mutein of the disclosure includes intramolecular disulfide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds.

It is, however, also possible to produce a mutein of the disclosure in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8).

However, a lipocalin mutein as described herein may not necessarily be generated or produced only by use of genetic engineering. Rather, such a mutein can also be obtained by chemical synthesis such as Merrifield solid phase polypeptide synthesis or by in vitro transcription and translation. It is for example possible that promising mutations are identified using molecular modeling and then to synthesize the wanted (designed) polypeptide in vitro and investigate the binding activity for CD137. Methods for the solid phase and/or solution phase synthesis of proteins are well known in the art (see e.g. Bruckdorfer, T. et al. (2004) *Curr. Pharm. Biotechnol.* 5, 29-43).

In another embodiment, the lipocalin muteins of the disclosure may be produced by in vitro transcription/translation employing well-established methods known to those skilled in the art.

The skilled worker will appreciate methods useful to prepare lipocalin muteins contemplated by the present disclosure but whose protein or nucleic acid sequences are not explicity disclosed herein. As an overview, such modifications of the amino acid sequence include, e.g., directed mutagenesis of single amino acid positions in order to simplify sub-cloning of a mutated lipocalin gene or its parts by incorporating cleavage sites for certain restriction enzymes. In addition, these mutations can also be incorporated to further improve the affinity of a lipocalin mutein for its target (e.g. CD137, respectively). Furthermore, mutations can be introduced to modulate certain characteristics of the mutein such as to improve folding stability, serum stability, protein resistance or water solubility or to reduce aggregation tendency, if necessary. For example, naturally occurring cysteine residues may be mutated to other amino acids to prevent disulphide bridge formation.

The lipocalin muteins disclosed herein and its derivatives can be used in many fields similar to antibodies or fragments thereof. For example, the lipocalin muteins can be used for labeling with an enzyme, an antibody, a radioactive substance or any other group having biochemical activity or defined binding characteristics. By doing so, their respective targets or conjugates or fusion proteins thereof can be detected or brought in contact with them. In addition, lipocalin muteins of the disclosure can serve to detect chemical structures by means of established analytical methods (e.g., ELISA or Western Blot) or by microscopy or immunosensorics. In this regard, the detection signal can either be generated directly by use of a suitable mutein conjugate or fusion protein or indirectly by immunochemical detection of the bound mutein via an antibody.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

VI. EXAMPLES

Example 1: Selection and Optimization of Muteins Specifically Binding to CD137

The representative CD137-specific lipocalin muteins disclosed in this application were selected from nave mutant libraries based on human NGAL and human TLc. Different strategies and targets were employed to obtain CD137-binding muteins. Recombinant targets utilized were the commercially available Fc-fusion of the full extracellular domain of CD137 from human (huCD137-Fc, R&D Systems 838-4B) and individual subdomains of human CD137, all generated as fusions to the human Fc fragment. As an alternative non-Fc fused target we employed the His-tagged human CD137 extracellular domain (Invitrogen, 10041-H08H-250). Alternatively, a cell-based panning using CHO cells transfected with the full cDNA of human CD137 was employed. Protein- and Cell-based pannings were performed using standard procedures. The clones obtained after selection were subjected to a screening process as described in Example 2.

Example 2: Identification of Muteins Specifically Binding to CD137 Using High-Throughput ELISA Screening Individual lipocalin muteins fused to a C-terminal Strep-tag (SEQ ID NO: 23, cf. Example 3) were used to inoculate 2×YT/Amp medium and grown overnight (14-18 h) to stationary phase. Subsequently, 50 µL 2×YT/Amp were inoculated from the stationary phase cultures and incubated for 3 h at 37° C. and then shifted to 22° C. until an $OD_{595}$ of 0.6-0.8 was reached. Production of muteins was induced by addition of 10 µL 2×YT/Amp supplemented with 1.2 µg/ml anhydrotetracyclin. Cultures were incubated at 22° C. until the next day. After addition of 40 µL of 5% (w/v) BSA in PBS/T and incubation for 1 h at 25° C. cultures were ready for use in screening assays.

Binding of the isolated muteins to human CD137 was tested by coating huCD137-Fc (5 µg/ml in PBS) of the relevant species overnight at 4° C. on microtiterplates. After blocking the plate with PBST containing 2% BSA, 20 µL of BSA-blocked cultures were added to the microtiter plates and incubated for 1 h at 25° C. Bound muteins were detected with anti-StrepTag antibody conjugated with horseradish peroxidase (1 h incubation; IBA, Goettingen). For quantification, 20 µL of QuantaBlu fluorogenic peroxidase substrate were added and the resulting fluorescence was determined at an excitation wavelength of 330 nM and an emission wavelength of 420 nM.

To select for muteins with increased temperature resistance, BSA-blocked cultures were incubated for 1 h at 60° C. and then allowed to cool down to room temperature before adding them to CD137 coated and BSA-blocked microtiterplates as described in the previous paragraph. The muteins were subsequently processed as described in the previous paragraph and were selected for bacterial expression, purification, and further characterization.

Example 3: Expression of Muteins

Unique muteins were expressed with C-terminal tag SAWSHPQFEK (SEQ ID NO: 21) or PSAWSHPQFEK (SEQ ID NO: 22); including an SA or PSA linker and Strep-tag® II, WSHPQFEK (SEQ ID NO: 23) in E. coli in 2YT-Amp medium to purify the muteins after expression using Streptactin affinity chromatography and preparative size exclusion chromatography. Finally, lipocalin muteins were subjected to an endotoxin depletion step utilizing Mustang E columns. Purified lipocalin muteins were then characterized as detailed in all following examples.

Example 4: Affinity of Muteins Binding to Human CD137-Fc Fusion Protein Determined by Surface Plasmon Resonance (SPR)

Surface plasmon resonance (SPR) was used to measure binding kinetics and affinity of the representative lipocalin muteins disclosed herein.

SPR analysis of the binding of the representative muteins to human CD137-Fc fusion protein (huCD137-Fc) was performed at 37° C. on a Biacore T200 instrument (GE Healthcare) using HBS-EP+(1×; BR-1006-69; GE Healthcare) as running buffer.

Prior to the protein measurements three regeneration cycles were performed for conditioning purposes. Regeneration of the derivatized chip surface was achieved by applying 3M $MgCl_2$ for 60 s followed by 10 mM glycine, pH 1.7 for 180 s. Anti-human IgG-Fc antibody was utilized to immobilize huCD137-Fc in a subsequent step and taken from the human antibody capture kit (GE Healthcare, BR-1008-39). It was immobilized on a CM5 sensor chip using standard amine coupling chemistry and the immobilization buffer included in the kit (10 mM sodium acetate pH 5.0), resulting in a ligand density of about 13000 resonance units (RU). The reference channel was treated accordingly.

HuCD137-Fc at a concentration of 0.5 µg/mL was captured on this surface for 180 s at a flow rate of 10 µL/min in HBS-EP+ buffer. No target protein was applied to the reference channel. Subsequently, the lipocalin muteins were applied in an appropriate dilution series in HBS-EP+ buffer at a flow rate of 30 µL/min. Regeneration of the derivatized chip surface was achieved as described above. Data were evaluated with Biacore T200 Evaluation software (V 2.0). Double referencing was used and the 1:1 Binding model was used to fit the raw data.

FIG. 1 shows the SPR traces and fit curves determined for the lipocalin muteins tested, with the corresponding SEQ ID NOs provided in the graphs. The data is depicted for the binding to huCD137-Fc. There are clear SPR binding signals towards the human target, while the negative controls SEQ ID NO: 3 and SEQ ID NO: 4 exhibit no binding. The affinities resulting from a fit of this data are provided in Table 1 below.

TABLE 1

| SEQ ID AA | KD huCD137 [nM] |
|---|---|
| SEQ ID NO: 5 | 162 |
| SEQ ID NO: 6 | 112 |
| SEQ ID NO: 7 | 110 |
| SEQ ID NO: 8 | 151 |
| SEQ ID NO: 9 | 209 |
| SEQ ID NO: 10 | 112 |
| SEQ ID NO: 11 | 269 |
| SEQ ID NO: 12 | 36 |
| SEQ ID NO: 13 | 2 |
| SEQ ID NO: 14 | 9 |
| SEQ ID NO: 15 | 23 |
| SEQ ID NO: 16 | 30 |
| SEQ ID NO: 17 | 50 |
| SEQ ID NO: 18 | 77 |
| SEQ ID NO: 19 | 98 |
| SEQ ID NO: 20 | 138 |
| SEQ ID NO: 3 (ctrl) | not binding |
| SEQ ID NO: 4 (ctrl) | not binding |

Example 5: Surface Plasmon Resonance (SPR) Assay to Determine Competition Between Human CD137L and Muteins in Binding to Human CD137-Fc Fusion Protein With respect to a lipocalin mutein described in this application that binds CD137, generally, two modes of binding are possible: in the first case, the mutein's binding site overlaps with the binding site of human CD137 ligand (CD137L) to CD137. When such lipocalin mutein binds to CD137, this interferes with binding of CD137L to CD137 and concomitantly leads to interference with natural CD137L signaling ("competitive binding"); in the second case, the mutein's binding site does not overlap with the CD137L's binding site and such lipocalin mutein can bind to CD137 without interfering with CD137L binding and natural CD137L signaling ("non-competitive binding").

Clustering of CD137 via its ligand activates the downstream signaling pathways of CD137. In the case of T-cells, CD137 activation leads to costimulation of the T-cell's activatory responses, such as proliferation and the production of proinflammatory cytokines.

Another way to induce CD137 clustering is to use immobilized CD137-binding agents. When coated on the plate (e.g. on a plastic culture dish and incubating the T-cells in the dish), both competitive and non-competitive CD137 binders achieve CD137 clustering and thereby activate downstream signaling.

Therefore, on the one hand, both competitive and non-competitive CD137 binders, when applied as described above, can activate the downstream signaling pathways of CD137.

A competitive CD137 binder, on the other hand, can be employed to inhibit the natural CD137/CD137L interaction, and thereby suppress the natural signaling induced by the encounter of CD137-positive cells with CD137L-expressing cells, for example, antigen-presenting cells. Such a mode of action is desirable in the cases where it is desired to suppress an inappropriately strong inflammatory or autoimmune reaction.

To demonstrate that this application provides both the competitive-type muteins and the non-competitive-type muteins, we employed a surface plasmon resonance (SPR) experiment. We used it to investigate the competition between CD137L and three representative lipocalin muteins disclosed herein in binding to the human CD137-Fc fusion protein (huCD137-Fc). In this assay, it is investigated whether a lipocalin mutein can bind to the preformed complex of CD137 and CD137L; if this is not the case, then this is evidence that the lipocalin mutein binding epitope on CD137 overlaps with the CD137L binding epitope on CD137. The respective mutein therefore binds to CD137 competitively with respect to the CD137/CD137L interaction. If both CD137L and the lipocalin mutein can bind at the same time, than the binding is non-competitive with respect to the CD137/CD137L interaction.

The competition assay was performed at 37° C. on a Biacore T200 instrument (GE Healthcare) using HBS-EP+ (1×; BR-1006-69; GE Healthcare) as running buffer. The Biotin CAPture Kit (GE Healthcare) was used to immobilize biotinylated huCD137-Fc to a chip surface. CD137-Fc proteins were biotinylated using standard NHS chemistry. Undiluted Biotin CAPture Reagent (streptavidin conjugated with ss-DNA oligo) was captured on a sensor chip CAP with the pre-immobilized complementary ss-DNA oligo. Thereafter, biotinylated CD137-Fc protein at 2 µg/mL was applied for 300 s at a flow rate of 5 µL/min. Regeneration of the chip surface was achieved by applying 6M guanidinium-HCl in 250 mM NaOH for 120 s at a flow rate of 10 µL/min.

In the two first measurement cycles, successful binding of CD137L to CD137 under the experimental conditions was ascertained, and the reference level for the individual binding of a tested lipocalin mutein in the absence of ligand was obtained. In the third cycle, CD137 was saturated with CD137L before the lipocalin mutein was added as described in detail as follows.

The human CD137 ligand-Fc (R&D Systems 2295-4L-025/CF) ligand was applied to the immobilized CD137-Fc protein at a concentration of 500 nM and a flow rate of 30 µL/min for 30 s. After regeneration, the lipocalin muteins were applied at a concentration of 5 µM at a flow rate of 30 µL/min for 30 s. Finally, after another regeneration cycle the human CD137 ligand-Fc was applied to the immobilized CD137-Fc proteins at a concentration of 500 nM for 30 s directly followed by the muteins at a concentration of 5 µM for 30 s both at a flow rate of 30 µL/min. Regeneration of the chip surface was achieved by applying 6M guanidinium-HCl in 250 mM NaOH for 120 s at a flow rate of 10 µL/min. The resulting sensorgrams were analyzed visually and it was determined whether bound CD137 ligand-Fc had an impact on the interaction of the muteins with the immobilized CD137-Fc proteins. The sensorgrams of the cycles were CD137 ligand-Fc interaction or muteins were applied alone served as controls.

Representative examples for the relevant segment of the resulting sensorgrams are provided in FIG. 2 for the muteins of SEQ ID NO: 5, SEQ ID NO: 12 and SEQ ID NO: 13. The SPR trace for the binding of the respective lipocalin mutein to huCD137-Fc alone is marked with an arrow with a solid stem. The SPR trace for the binding of the lipocalin mutein to huCD137-Fc that has been saturated with CD137L is marked with an arrow with a broken stem. The data shows that the mutein of SEQ ID NO: 5 for example can not bind to huCD137-Fc in the presence of CD137L (FIG. 2A). In contrast, both the mutein of SEQ ID NO: 12 and the mutein of SEQ ID NO: 13 bind to huCD137-Fc with a very similar response both in the absence and presence of CD137L, showing that there is no competition in the binding between the lipocalin muteins and CD137L. This data is summarized in Table 2.

TABLE 2

| SEQ ID AA | Mode of binding |
| --- | --- |
| SEQ ID NO: 5 | competitive |
| SEQ ID NO: 12 | non-competitive |
| SEQ ID NO: 13 | non-competitive |

Example 6: FACS Analysis of Lipocalin Muteins Binding to Cells Expressing Human CD137

We employed FACS studies in order to assess the specific binding of lipocalin muteins and negative controls to chinese hamster ovary (CHO) cells stably transfected with human CD137 (CHO-huCD137). The cell line was generated using the Flp-In system (Invitrogen) according to the manufacturer's instructions. Mock-transfected Flp-In CHO cells served as the negative control.

Tranfected CHO cells were maintained in Ham's F12 medium (Invitrogen) supplemented with 10% Fetal Calf Serum (FCS, Biochrom) and 500 µg/ml Hygromycin B (Roth). Cells were cultured in cell culture flasks under standard conditions according to manufacturer's instruction (37° C., 5% CO2 atmosphere). In order to dissociate the adherent cells for subculture or FACS experiments, Accutase (PAA) was employed according to the manufacturer's instructions.

To perform the experiment, CD137-positive and negative Flp-In CHO cells were incubated with lipocalin muteins, and bound mutein was labeled using anti-lipocalin primary antibodies and fluorescently labeled secondary antibodies, which were detected by FACS analysis as described in the following.

1×10⁵ cells per well were pre-incubated for 1 h in ice-cold PBS containing 5% fetal calf serum (PBS-FCS). Subsequently, a dilution series of lipocalin muteins and negative controls typically ranging from 10 µM to 1 nM was added to the cells and incubation was continued on ice for 1 h. Cells were washed twice in ice-cold PBS using centrifugation at 300 g and then incubated with a rabbit anti-lipocalin primary antibody (Pieris, (polyclonal rabbit anti-hNGAL and rabbit anti-hTLC; Pieris) for 30 min on ice. Cells were washed twice in ice-cold PBS, re-suspended in PBS-FCS and incubated 30 min on ice with a secondary anti-rabbit antibody labelled with the fluorescent dye Alexa488 (Life Technologies). Cells were subsequently washed and analyzed using a Guava easyCyte HT Flow cytometer. Typically, a gate was set to exclude non-viable cells and 5.000 events were recorded. Numerical results are expressed as the geometric mean of the fluorescence intensity.

FACS histograms for all clones tested are provided in FIG. 3. In the respective plots, the SEQ ID NOs of the respective lipocalin muteins are depicted. In line with the SPR data (FIG. 1, Table 1), all muteins show a clear binding to cell-expressed CD137. The EC50 resulting from a fit of this data are provided in Table 2 below.

TABLE 2

| SEQ ID AA | EC50 CHO::hCD137 [nM] |
|---|---|
| SEQ ID NO: 6 | 61.1 |
| SEQ ID NO: 7 | 67.6 |
| SEQ ID NO: 8 | 234.6 |
| SEQ ID NO: 9 | 113.3 |
| SEQ ID NO: 11 | 53 |
| SEQ ID NO: 13 | 4.3 |
| SEQ ID NO: 14 | 4.5 |
| SEQ ID NO: 15 | 7.8 |
| SEQ ID NO: 17 | 17.9 |
| SEQ ID NO: 18 | 13.7 |
| SEQ ID NO: 20 | 18 |
| SEQ ID NO: 3 (ctrl) | no binding |
| SEQ ID NO: 4 (ctrl) | no binding |

Example 7: Functional T-Cell Activation Assay Using Coated Lipocalin Muteins

We employed a T-cell activation assay to assess the ability of a set of representative CD137-binding lipocalin muteins to co-stimulate T-cell responses. The tested muteins (SEQ ID NO: 13, SEQ ID NO: 14, and SEQ ID NO: 15) span an SPR affinity ranging from 2 nM to >23 nM in Example 4 (cf. Table 1). As discussed in Example 5, there are several ways to induce CD137 clustering and in this experiment we applied immobilized CD137-binding agents. In this experiment, the lipocalin muteins were coated onto a plastic dish together with an anti-human CD3 antibody (Muronomab, Janssen-Cilag) and purified T-cells were subsequently incubated on the coated surface in the presence of soluble anti-human CD28 antibody (Clone 28.2; eBioscience). Anti-CD3 and anti-CD28 antibodies were used to provide a sub-threshhold stimulus to the T-cells that could be costimulated by CD137 costimulation. As a readout, we measured supernatant interleukin 2 (IL-2) levels. An increased IL-2 production is one of the hallmarks of T-cell activation, and the increase in IL-2 levels by costimulation with an anti-CD137 antibody has been described in the literature (Fisher T. S. et al., Cancer Immunol Immunother (2012) 61:1721-1733). As a negative control, SEQ ID NO: 4 was utilized. In the following, we provide a detailed description of the experiment.

Human peripheral blood mononuclear cells (PBMC) from healthy volunteer donors were isolated from buffy coats by centrifugation through a Polysucrose density gradient (Biocoll 1.077 g/mL from Biochrom), following Biochrom's protocols. The T lymphocytes were isolated from the resulting PBMC using a Pan T-cell purification Kit (Miltenyi Biotec GmbH) and the manufacturer's protocols, Purified T-cells were resuspended in a buffer consisting of 90% FCS and 10% DMSO, immediately frozen down using liquid nitrogen and stored in liquid nitrogen until further use. For the assay, T cells were thawed for 16 h and cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were coated overnight at 4° C. using 200 µL of a mixture of 0.5 µg/mL anti-CD3 antibody and 25 µg/mL rabbit anti-lipocalin antibodies (polyclonal rabbit anti-hNGAL, Pieris). The latter was employed to allow for immobilization of lipocalin muteins by affinity capturing. The following day, wells were washed twice with PBS, and 50 µL of CD137-binding lipocalin muteins of SEQ ID NO: 13, SEQ ID NO: 14 and SEQ ID NO: 15, all at a concentration of 25 µg/mL, were captured on the precoated plates for 1 h at 37° C. SEQ ID NO: 4 was employed likewise and served as the negative control. After again washing twice with PBS, 100 µL of the T-cell suspension (corresponding to 5×10⁴ T cells) in culture media supplemented with 2 µg/mL hCD28 antibody was added to each well. Plates were covered with a gas permeable seal (4titude) and incubated at 37° C. in a humidified 5% CO2 atmosphere for 3 days. Subsequently, IL-2 in the supernatant was assessed.

Human IL-2 levels in the pooled cell culture supernatants were quantified using the IL-2 DuoSet kit from R&D Systems. In the first step, a 384 well plate was coated at room temperature for 2 h with 1 µg/mL "Human IL-2 Capture Antibody" (R&D System) diluted in PBS. Subsequently, wells were washed 5 times with 80 µL PBS-T (PBS containing 0.05% Tween20) using a Biotek EL405 select CW washer (Biotek). After 1 h blocking in PBS-T additionally containing 1% casein (w/w), pooled supernatant and a concentration series of an IL-2 standard diluted in culture medium were incubated in the 384-well plate overnight at 4° C. To allow for detection and quantitation of captured IL-2, a mixture of 100 ng/mL biotinylated goat anti-hIL-2-Bio detection antibody (R&D System) and 1 µg/mL Sulfotag-labelled streptavidin (Mesoscale Discovery) wer added in PBS-T containing 0.5% casein and incubated at room temperature for 1 h. After washing, 25 µL reading buffer was added to each well and the electrochemiluminescence (ECL) signal of every well was read using a Mesoscale Discovery reader. Analysis and quantification were performed using Mesoscale Discovery software.

The resulting data is plotted in FIG. 4A. There is a clearly increased IL-2 concentration in the supernatant due to T-cell activation for the lipocalin muteins of SEQ ID NO: 13, SEQ ID NO: 14 and SEQ ID NO: 15 compared to the negative control of SEQ ID NO: 4. The experiment indicates that, all muteins tested are able to costimulate a T-cell response when coated on a plastic culture dish.

Example 8: Functional T-Cell Activation Assay Using Lipocalin Muteins in Solution To test whether representative lipocalin muteins also activate CD137 by simple binding without clustering, the assay of Example 7 was carried out in an analogous fashion to Example 5, but using soluble instead of captured lipocalin muteins. In this assay, flat-bottom tissue culture plates were coated as described above, but using anti-CD3 antibody only. Plates were processed as described above until after the T-cell addition step (including 2 µg/mL hCD28), which was followed by the addition of 50 µL of the lipocalin muteins in solution at a concentration of 25 µg/mL.

The resulting data is plotted in FIG. 4B. There is no significant increase in IL-2 concentration in the supernatant due to T-cell activation for any of the lipocalin muteins tested compared to the negative control of SEQ ID NO: 4. The experiment indicates that monomeric lipocalin muteins in solution, at a concentration that is sufficient to saturate all CD137 receptors, do not costimulate T-cells.

Example 9: Functional T-Cell Activation Assay Using Coated Lipocalin Muteins To investigate in more detail the ability of mutein of SEQ ID NO: 13 to costimulate T-cell responses, we employed a T-cell activation assay as in Example 7. As readouts, we assessed continued proliferation of the T-cells after three days incubation using a 4 h BrdU pulse, and measured supernatant IL-2 and Interferon gamma (IFN-glevels. Beside proliferation and IL-2 production, an increased IFN-g production is a further hallmark of T-cell activation, and the increase in IFN-γ levels by costimulation with an anti-CD137 antibody has been described in the literature (Jure-Kunkel, M. et al., U.S. Pat. No. 7,288,638).

As a negative control, the wild-type like lipocalin mutein SEQ ID NO: 4 was utilized. This experiment was, in some aspects, carried out in an identical manner to the experiment described in Example 8. In the following, we provide a detailed description of the experiment.

Human peripheral blood mononuclear cells (PBMC) from healthy volunteer donors were isolated from buffy coats by centrifugation through a Polysucrose density gradient (Biocoll 1.077 g/mL from Biochrom), following Biochrom's protocols. The T lymphocytes were isolated from the resulting PBMC using a Pan T-cell purification Kit (Miltenyi Biotec GmbH) and the manufacturer's protocols. Purified T-cells were resuspended in a buffer consisting of 90% FCS and 10% DMSO, immediately frozen down using liquid nitrogen and stored in liquid nitrogen until further use. For the assay, T-cells were thawed for 16 h and cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were coated overnight at 4° C. using 200 µL of a mixture of 5 µg/mL anti-CD3 antibody and 25 µg/mL rabbit anti-lipocalin-scaffold antibody (polyclonal rabbit anti-hNGAL, Pieris). The latter was employed to allow for immobilization of SEQ ID NO: 13 by affinity capturing. As a negative control, an IgG1 isotype control was coated at 5 µg/mL instead of the anti-CD3 antibody, together with. the 25 µg/mL rabbit anti-lipocalin-scaffold antibody. The following day, wells were washed twice with PBS, and 50 µL of a dilution series of SEQ ID NO: 13 ranging from 50 µg/mL to 0.8 µg/mL in seven steps was captured on the precoated plates for 1 h at 37° C. As a negative control, SEQ ID NO: 4 was captured at three concentrations (50 µg/mL, 25 µg/mL, 12.5 µg/mL). As a further negative control, SEQ ID NO: 13 was captured at 50 µg/mL to the wells that had been coated with IgG1 isotype and the anti-hNGAL capture antibody (see above). After again washing twice with PBS, 100 µL of the T-cell suspension (corresponding to $5 \times 10^4$ T cells) in culture media was added to the wells. This was performed either in the presence or absence of hCD28 antibody at a concentration of 2 µg/mL. Plates were covered with a gas permeable seal (4titude) and incubated at 37° C. in a humidified 5% CO2 atmosphere for 3 days. Subsequently, IL-2 and IFN-γ concentration in the supernatant, as well as cell proliferation were assessed.

In order to quantify T-cell proliferation, the chemiluminescent cell proliferation ELISA kit based on BrdU incorporation (Roche) was used according to the manufacturer's instructions. Briefly, on day 3, 10 µL of BrdU labeling solution were added to each well and proliferation was allowed to proceed for a further 4 h at 37° C. under a humidified 5% CO2 atmosphere. Plates were centrifuged at 300 g for 10 min and supernatants of the triplicates were pooled and immediately stored at −20° C. for later IL-2 and IFN-γ quantification. Plates were subsequently dried at 60° C. for 1 hour. 200 µL of "FixDenat" solution were added to each well and the plates were incubated at room temperature for 30 min. Incorporated BRDU was labeled with a peroxidase-labelled anti-BrdU antibody by 2 h incubation at room temperature. BrdU levels were assessed by quantifying a chemiluminescent peroxidase-catalysed reaction in a PheraStar FS reader.

Human IL-2 and IFN-γ levels in the pooled cell culture supernatants were quantified using the IL-2 DuoSet and IFN-γ DuoSet kits from R&D Systems. The procedure is carried out analogously for both cytokines, and described only for IL-2 in the following. In the first step, a 384 well plate was coated at room temperature for 2 h with 1 µg/mL "Human IL-2 Capture Antibody" (R&D System) diluted in PBS. Subsequently, wells were washed 5 times with 80 µL PBS-T (PBS containing 0.05% Tween20) using a Biotek EL405 select CW washer (Biotek). After 1 h blocking in PBS-T additionally containing 1% casein (w/w), pooled supernatant and a concentration series of an IL-2 standard diluted in culture medium were incubated in the 384-well plate overnight at 4° C. To allow for detection and quantitation of captured IL-2, a mixture of 100 ng/mL biotinylated goat anti-hIL-2-Bio detection antibody (R&D System) and 1 µg/mL Sulfotag-labelled streptavidin (Mesoscale Discovery) wer added in PBS-T containing 0.5% casein and incubated at room temperature for 1 h. After washing, 25 µL reading buffer was added to each well and the electrochemiluminescence (ECL) signal of every well was read using a Mesoscale Discovery reader. Analysis and quantification were performed using Mesoscale Discovery software.

The result of the experiment is depicted in FIG. 5. Readouts of proliferation, IL-2 and IFN-γ in the supernatant for the experiment using both anti-CD3 and anti-CD28 antibodies are provided in FIGS. 5A, 5C and 5E, respectively. The same readouts for the experiment performed with anti-CD3 antibody only are provided in FIGS. 5B, 5D and 5F.

In the experiment employing stimulation by anti-CD3 and anti-CD28 antibodies, there is a clear dose-dependent increase in proliferation rate (FIG. 5A), which is up to 14-fold higher than for the negative control of SEQ ID NO: 4. Proliferation in the absence of anti-CD3 mAb (column labeled as "IgG1") is negligible. Regarding IL-2 production (FIG. 5C), there is also a clear dose-dependent increase that levels at a maximum response at a coating concentration of SEQ ID NO: 13 of 6.25 µg/mL and at higher concentrations remains constantly at levels of up to around 6fold compared to the negative control. Regarding IFN-γ production (FIG. 5E), the pattern is very similar, with maximum IFN-g levels reaching up to 2.5-fold values compared to the negative control.

In the experiment employing stimulation by anti-CD3 mAb only, we again find a clear dose-dependent increase in proliferation rate (FIG. 5A), which is up to 4-fold higher than for the negative control of SEQ ID NO: 4. There appears to be a maximum response at 6.25 µg/mL coating concentration of SEQ ID NO: 13, which reaches a 15-fold value compared to the negative control. At both higher and lower concentrations, the response is less pronounced. Regarding IFN-γ production, there is a dose-dependent increase that levels at a maximum response at a coating concentration of SEQ ID NO: 13 of 6.25 µg/mL and at higher concentrations remains constantly at levels of up to around 2.5-fold compared to the negative control.

Overall, the experiment shown in this Example 9 clearly demonstrates a significant costimulation of T-cell response by the mutein of SEQ ID NO: 13 with regard to proliferation, IL-2 production and IFN-γ production, both in the presence and in the absence of CD28 stimulation.

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

Equivalents: Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

The invention claimed is:

1. A nucleic acid molecule comprising a nucleotide sequence encoding a mutein of human Lipocalin 2 (hNGAL) that binds CD137, wherein the mutein comprises at least 10 of the following mutated amino acid residues in comparison with the linear polypeptide sequence of mature hNGAL (SEQ ID NO: 2): Gln 28→His; Leu 36→Gln; Ala 40→Ile; Ile 41→Arg or Lys; Gln 49→Val, Ile, His, Ser or Asn; Tyr 52→Met; Asn 65→Asp; Ser 68→Met, Ala or Gly; Leu 70→Ala, Lys, Ser or Thr; Arg 72→Asp; Lys 73→Asp; Asp 77→Met, Arg, Thr or Asn; Trp 79→Ala or Asp; Arg 81→Met, Trp or Ser; Phe 83→Leu; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu; and Lys 134→Tyr, and wherein the mutein comprises an amino acid sequence selected from the group consisting of SEQ ID NOs: 12-20.

2. The nucleic acid molecule of claim 1, wherein the mutein binds CD137 with an affinity measured by a dissociation constant (KD) of about 150 nM or lower.

3. The nucleic acid molecule of claim 1, wherein the mutein binds CD137 with an affinity measured by a KD of about 10 nM or lower.

4. The nucleic acid molecule of claim 1, wherein the mutein binds CD137 with an affinity measured by a half maximal effective concentration (EC50) value of about 18 nM or lower.

5. The nucleic acid molecule of claim 1, wherein the mutein does not interfere with the binding of CD137L to CD137.

6. The nucleic acid molecule of claim 1, wherein the mutein is capable of enhancing IL-2 secretion.

7. The nucleic acid molecule of claim 1, wherein the mutein is capable of increasing IFN-gamma production.

8. A host cell containing the nucleic acid molecule of claim 1, wherein the host cell is a prokaryotic cell selected from the group consisting of Escherichia coli (E. coli) and Bacillus subtilis.

9. A host cell containing the nucleic acid molecule of claim 1, wherein the host cell is a eukaryotic cell selected from the group consisting of Saccharomyces cerevisiae, Pichia pastoris, SF9 or High5 insect cells and immortalized mammalian cell lines.

10. The host cell of claim 9, wherein the immortalized mammalian cell lines are Hela cells or CHO cells.

11. A host cell containing the nucleic acid molecule of claim 1, wherein the host cell is a primary mammalian cell.

12. A host cell containing the nucleic acid molecule of claim 1.

13. The host cell of claim 12, wherein the host cell is a prokaryotic cell selected from the group consisting of Escherichia coli (E. coli) and Bacillus subtilis or the host cell is a eukaryotic cell selected from the group consisting of Saccharomyces cerevisiae, Pichia pastoris, SF9 or High5 insect cells and immortalized mammalian cell lines.

14. A nucleic acid molecule comprising a nucleotide sequence encoding a mutein of human Lipocalin 2 (hNGAL) that binds CD137, wherein the mutein comprises at least 10 of the following mutated amino acid residues in comparison with the linear polypeptide sequence of mature hNGAL (SEQ ID NO: 2): Gln 28→His; Leu 36→Gln; Ala 40→Ile; Ile 41→Arg or Lys; Gln 49→Val, Ile, His, Ser or Asn; Tyr 52→Met; Asn 65→Asp; Ser 68→Met, Ala or Gly; Leu 70→Ala, Lys, Ser or Thr; Arg 72→Asp; Lys 73→Asp; Asp 77→Met, Arg, Thr or Asn; Trp 79→Ala or Asp; Arg 81→Met, Trp or Ser; Phe 83→Leu; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu; and Lys 134→Tyr, and wherein the mutein comprises an amino acid sequence having at least 95% sequence identity to the amino acid sequence shown in SEQ ID NO: 13.

15. The nucleic acid molecule of claim 14, wherein the mutein has the amino acid sequence of SEQ ID NO: 13.

16. A host cell containing the nucleic acid molecule of claim 14.

17. The host cell of claim 16, wherein the host cell is a prokaryotic cell selected from the group consisting of *Escherichia coli* (*E. coli*) and *Bacillus subtilis* or the host cell is a eukaryotic cell selected from the group consisting of *Saccharomyces cerevisiae, Pichia pastoris*, SF9 or High5 insect cells and immortalized mammalian cell lines.

\* \* \* \* \*

SEQUENCE LISTING

```
<160> NUMBER OF SEQ ID NOS: 39

<210> SEQ ID NO 1
<211> LENGTH: 156
<212> TYPE: PRT
<213> ORGANISM: artificial
<220> FEATURE:
<223> OTHER INFORMATION: wildtype human Tlc

<400> SEQUENCE: 1

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
    50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110
```

-continued

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly
145                 150                 155

<210> SEQ ID NO 2
<211> LENGTH: 178
<212> TYPE: PRT
<213> ORGANISM: artificial
<220> FEATURE:
<223> OTHER INFORMATION: wildtype hNGAL

<400> SEQUENCE: 2

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 3
<211> LENGTH: 152
<212> TYPE: PRT
<213> ORGANISM: artificial
<220> FEATURE:
<223> OTHER INFORMATION: negative control

<400> SEQUENCE: 3

Ala Ser Asp Glu Glu Ile Gln Asp Val Ser Gly Thr Trp Tyr Leu Lys
1               5                   10                  15

Ala Met Thr Val Asp Arg Glu Cys Pro Glu Met Asn Leu Glu Ser Val
            20                  25                  30

Thr Pro Met Thr Leu Thr Thr Leu Glu Gly Gly Asn Leu Glu Ala Lys
        35                  40                  45

Val Thr Met Leu Ile Ser Gly Arg Ser Gln Glu Val Lys Ala Val Leu
    50                  55                  60

Glu Lys Thr Asp Glu Pro Gly Lys Tyr Thr Ala Asp Gly Gly Lys His
65                  70                  75                  80

-continued

Val Ala Tyr Ile Ile Arg Ser His Val Lys Asp His Tyr Ile Phe Tyr
                    85                  90                  95

Ser Glu Gly Glu Cys His Gly Lys Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
130                 135                 140

Gln Ser Glu Thr Ser Ser Pro Gly
145                 150

<210> SEQ ID NO 4
<211> LENGTH: 178
<212> TYPE: PRT
<213> ORGANISM: artificial
<220> FEATURE:
<223> OTHER INFORMATION: negative control

<400> SEQUENCE: 4

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Leu Ala Gly Asn Ala Ile Leu Arg Glu Asp Lys Asp Pro
                35                  40                  45

Gln Lys Met Tyr Ala Thr Ile Tyr Glu Leu Lys Glu Asp Lys Ser Tyr
            50                  55                  60

Asn Val Thr Ser Val Leu Phe Arg Lys Lys Lys Cys Asp Tyr Trp Ile
65                  70                  75                  80

Arg Thr Phe Val Pro Gly Ser Gln Pro Gly Glu Phe Thr Leu Gly Asn
                    85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 5
<211> LENGTH: 152
<212> TYPE: PRT
<213> ORGANISM: artificial
<220> FEATURE:
<223> OTHER INFORMATION: lipocalin mutein

<400> SEQUENCE: 5

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
                20                  25                  30

Thr Pro Met Thr Leu Thr Thr Leu Glu Gly Gly Asn Leu Glu Ala Lys
                35                  40                  45

Val Thr Met Ala Ile Asp Gly Pro Ala Gln Glu Val Lys Ala Val Leu
            50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
            115                 120                 125

Ala Ala Gly Ala Arg Gly Leu Ser Thr Glu Ser Ile Leu Ile Pro Arg
            130                 135                 140

Gln Ser Glu Thr Ser Ser Pro Gly
145                 150

<210> SEQ ID NO 6
<211> LENGTH: 152
<212> TYPE: PRT
<213> ORGANISM: artificial
<220> FEATURE:
<223> OTHER INFORMATION: lipocalin mutein

<400> SEQUENCE: 6

Thr Ser Asp Glu Glu Ile Gln Asp Val Ser Gly Thr Trp Tyr Leu Lys
  1               5                  10                  15

Ala Met Thr Val Asp Glu Gly Cys Arg Pro Trp Asn Ile Phe Ser Val
                 20                  25                  30

Thr Pro Met Thr Leu Thr Thr Leu Glu Gly Gly Asn Leu Glu Ala Lys
            35                  40                  45

Val Thr Met Ala Ile Asp Gly Pro Ala Gln Glu Val Arg Ala Val Leu
            50                  55                  60

Glu Lys Thr Asp Glu Pro Gly Lys Tyr Thr Ala Asp Gly Gly Lys His
 65                  70                  75                  80

Asp Ala Tyr Ile Ile Arg Ser His Val Lys Asp His Tyr Ile Phe Tyr
                 85                  90                  95

Ser Glu Gly Val Cys Asp Gly Ser Pro Val Pro Gly Val Trp Leu Val
            100                 105                 110

Gly Arg Asp Pro Glu Asn Asn Leu Glu Ala Leu Glu Asp Phe Glu Lys
            115                 120                 125

Thr Ala Gly Ala Arg Gly Leu Ser Thr Glu Ser Ile Leu Ile Pro Arg
            130                 135                 140

Gln Ser Glu Thr Ser Ser Pro Gly
145                 150

<210> SEQ ID NO 7
<211> LENGTH: 152
<212> TYPE: PRT
<213> ORGANISM: artificial
<220> FEATURE:
<223> OTHER INFORMATION: lipocalin mutein

<400> SEQUENCE: 7

Ala Ser Asp Glu Glu Ile Gln Asp Val Ser Gly Thr Trp Tyr Leu Lys
  1               5                  10                  15

Ala Met Thr Val Asp Glu Gly Cys Arg Pro Trp Asn Ile Phe Ser Val
                 20                  25                  30

Thr Pro Met Thr Leu Thr Thr Leu Glu Gly Gly Asn Leu Glu Ala Lys 35                  40                  45

Val Thr Met Ala Ile Asp Gly Pro Ala Gln Glu Val Asn Ala Val Leu
 50                  55                  60

Glu Lys Thr Asp Glu Pro Gly Lys Tyr Thr Ala Asp Gly Lys His
 65                  70                  75                  80

Val Ala Tyr Ile Ile Arg Ser His Val Arg Asp His Tyr Ile Phe Tyr
                 85                  90                  95

Ser Glu Gly Val Cys Asp Gly Ser Pro Val Pro Gly Val Trp Leu Val
                100                 105                 110

Gly Arg Asp Pro Glu Asn Asn Leu Glu Ala Leu Glu Asp Phe Glu Lys
                115                 120                 125

Thr Ala Gly Ala Arg Gly Leu Ser Thr Glu Ser Ile Leu Ile Pro Arg
            130                 135                 140

Gln Ser Glu Thr Ser Ser Pro Gly
145                 150

<210> SEQ ID NO 8
<211> LENGTH: 152
<212> TYPE: PRT
<213> ORGANISM: artificial
<220> FEATURE:
<223> OTHER INFORMATION: lipocalin mutein

<400> SEQUENCE: 8

Val Ser Asp Glu Glu Ile Gln Asp Val Ser Gly Thr Trp Tyr Leu Lys
 1               5                  10                  15

Ala Met Thr Val Asp Glu Gly Cys Arg Pro Trp Asn Ile Phe Ser Val
                20                  25                  30

Thr Pro Met Thr Leu Thr Thr Leu Glu Gly Gly Asn Leu Glu Ala Lys
            35                  40                  45

Val Thr Met Ala Ile Asp Gly Pro Ala Gln Glu Val Arg Ala Val Leu
 50                  55                  60

Glu Lys Thr Asp Glu Pro Gly Lys Tyr Thr Ala Asp Gly Lys His
 65                  70                  75                  80

Val Ala Tyr Ile Ile Arg Ser His Val Glu Asp His Tyr Ile Phe Tyr
                 85                  90                  95

Ser Glu Gly Val Cys Asp Gly Ser Pro Val Pro Gly Val Trp Leu Val
                100                 105                 110

Gly Arg Asp Pro Glu Asn Asn Leu Glu Ala Leu Glu Asp Phe Glu Lys
                115                 120                 125

Thr Ala Gly Ala Arg Gly Leu Ser Thr Glu Ser Ile Leu Ile Pro Arg
            130                 135                 140

Gln Ser Glu Thr Ser Ser Pro Gly
145                 150

<210> SEQ ID NO 9
<211> LENGTH: 152
<212> TYPE: PRT
<213> ORGANISM: artificial
<220> FEATURE:
<223> OTHER INFORMATION: lipocalin mutein

<400> SEQUENCE: 9

Ala Ser Asp Glu Glu Ile Gln Asp Val Ser Gly Thr Trp Tyr Leu Lys
 1               5                  10                  15

Ala Met Thr Val Asp Glu Gly Cys Arg Pro Trp Asn Ile Phe Ser Val
                20                  25                  30

```
Thr Pro Met Thr Leu Ser Thr Leu Glu Gly Gly Asn Leu Glu Ala Lys
            35                  40                  45

Val Thr Met Ala Ile Asp Gly Pro Ala Gln Glu Val Lys Ala Val Leu
 50                  55                  60

Glu Lys Thr Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly Val Cys Asp Gly Ser Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
130                 135                 140

Gln Ile Glu Thr Ser Ser Pro Gly
145                 150
```

<210> SEQ ID NO 10
<211> LENGTH: 152
<212> TYPE: PRT
<213> ORGANISM: artificial
<220> FEATURE:
<223> OTHER INFORMATION: lipocalin mutein

<400> SEQUENCE: 10

```
Ala Ser Asp Glu Glu Ile Gln Asp Val Ser Gly Thr Trp Tyr Leu Lys
 1               5                  10                  15

Ala Met Thr Val Asp Glu Gly Cys Arg Pro Trp Asn Ile Phe Ser Val
                 20                  25                  30

Thr Pro Met Thr Leu Thr Thr Leu Glu Gly Gly Asn Leu Glu Ala Glu
            35                  40                  45

Val Thr Met Ala Ile Asp Gly Pro Ala Gln Glu Val Lys Ala Val Leu
 50                  55                  60

Glu Lys Ala Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly Val Cys Asp Gly Ser Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Thr Ala Gly Ala Arg Gly Leu Ser Thr Glu Ser Ile Leu Ile Pro Ser
130                 135                 140

Gln Ile Glu Thr Ser Ser Pro Gly
145                 150
```

<210> SEQ ID NO 11
<211> LENGTH: 152
<212> TYPE: PRT
<213> ORGANISM: artificial
<220> FEATURE:
<223> OTHER INFORMATION: lipocalin mutein

<400> SEQUENCE: 11

```
Thr Ser Asp Glu Glu Ile Gln Asp Val Ser Gly Thr Trp Tyr Leu Lys
 1               5                  10                  15

Ala Met Thr Val Asp Glu Gly Cys Arg Pro Trp Asn Ile Phe Ser Val
                 20                  25                  30
```

```
Thr Pro Met Thr Leu Thr Thr Leu Glu Asp Gly Asn Leu Glu Ala Lys
         35                  40                  45

Val Thr Met Ala Ile Asp Gly Pro Ala Gln Glu Val Lys Ala Val Leu
 50                  55                  60

Glu Lys Ala Asp Glu Pro Gly Lys Tyr Thr Ala Asp Gly Gly Lys His
 65                  70                  75                  80

Val Ala Tyr Ile Ile Arg Ser His Val Lys Asp His Tyr Ile Phe Tyr
                 85                  90                  95

Ser Glu Gly Val Cys Asp Gly Ser Pro Val Pro Gly Val Trp Leu Val
                100                 105                 110

Gly Arg Asp Pro Lys Asn Asn Leu Glu Ala Leu Glu Asp Phe Glu Lys
                115                 120                 125

Ala Ala Gly Ala Arg Gly Leu Ser Thr Glu Ser Ile Leu Ile Pro Arg
130                 135                 140

Gln Ile Glu Thr Ser Ser Pro Gly
145                 150
```

<210> SEQ ID NO 12
<211> LENGTH: 178
<212> TYPE: PRT
<213> ORGANISM: artificial
<220> FEATURE:
<223> OTHER INFORMATION: lipocalin mutein

<400> SEQUENCE: 12

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe His Gly Lys Trp Tyr
                 20                  25                  30

Val Val Gly Gln Ala Gly Asn Ile Lys Leu Arg Glu Asp Lys Asp Pro
             35                  40                  45

Asn Lys Met Met Ala Thr Ile Tyr Glu Leu Lys Glu Asp Lys Ser Tyr
 50                  55                  60

Asn Val Thr Gly Val Thr Phe Asp Asp Lys Lys Cys Thr Tyr Ala Ile
 65                  70                  75                  80

Ser Thr Phe Val Pro Gly Ser Gln Pro Gly Glu Phe Thr Leu Gly Lys
                 85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
                115                 120                 125

Asn Arg Glu Glu Phe Tyr Ile Thr Leu Tyr Gly Arg Thr Lys Glu Leu
                130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 13
<211> LENGTH: 178
<212> TYPE: PRT
<213> ORGANISM: artificial
<220> FEATURE:
<223> OTHER INFORMATION: lipocalin mutein

<400> SEQUENCE: 13

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
            35                  40                  45

Ile Lys Met Met Ala Thr Ile Tyr Glu Leu Lys Glu Asp Lys Ser Tyr
50                  55                  60

Asp Val Thr Met Val Lys Phe Asp Asp Lys Lys Cys Met Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 14
<211> LENGTH: 178
<212> TYPE: PRT
<213> ORGANISM: artificial
<220> FEATURE:
<223> OTHER INFORMATION: lipocalin mutein

<400> SEQUENCE: 14

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
            35                  40                  45

Asn Lys Met Met Ala Thr Ile Tyr Glu Leu Lys Glu Asp Lys Ser Tyr
50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175
```

-continued

Asp Gly

<210> SEQ ID NO 15
<211> LENGTH: 178
<212> TYPE: PRT
<213> ORGANISM: artificial
<220> FEATURE:
<223> OTHER INFORMATION: lipocalin muein

<400> SEQUENCE: 15

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 16
<211> LENGTH: 175
<212> TYPE: PRT
<213> ORGANISM: artificial
<220> FEATURE:
<223> OTHER INFORMATION: lipocalin mutein

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Ser Lys Met
        35                  40                  45

Met Ala Thr Ile Tyr Glu Leu Lys Glu Asp Lys Ser Tyr Asp Val Thr
        50                  55                  60

Gly Val Ser Phe Asp Asp Lys Lys Cys Thr Tyr Ala Ile Met Thr Phe
65                  70                  75                  80

Val Pro Gly Ser Gln Pro Gly Glu Phe Thr Leu Gly Lys Ile Lys Ser
                85                  90                  95

Phe Pro Gly His Thr Ser Ser Leu Val Arg Val Val Ser Thr Asn Tyr
            100                 105                 110

Asn Gln His Ala Met Val Phe Phe Lys Phe Val Phe Gln Asn Arg Glu

```
                    115                 120                 125
Glu Phe Tyr Ile Thr Leu Tyr Gly Arg Thr Lys Glu Leu Thr Ser Glu
                130                 135                 140
Leu Lys Glu Asn Phe Ile Arg Phe Ser Lys Ser Leu Gly Leu Pro Glu
145                 150                 155                 160
Asn His Ile Val Phe Pro Val Pro Ile Asp Gln Cys Ile Asp Gly
                165                 170                 175
```

<210> SEQ ID NO 17
<211> LENGTH: 178
<212> TYPE: PRT
<213> ORGANISM: artificial
<220> FEATURE:
<223> OTHER INFORMATION: lipocalin mutein

<400> SEQUENCE: 17

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
                20                  25                  30
Val Val Gly Gln Ala Gly Asn Ile Lys Leu Arg Glu Asp Lys Asp Pro
            35                  40                  45
Val Lys Met Met Ala Thr Ile Tyr Glu Leu Lys Glu Asp Lys Ser Tyr
        50                  55                  60
Asp Val Thr Gly Val Thr Phe Asp Lys Lys Cys Arg Tyr Asp Ile
65                  70                  75                  80
Ser Thr Phe Val Pro Gly Ser Gln Pro Gly Glu Phe Thr Phe Gly Lys
                85                  90                  95
Ile Lys Ser Phe Pro Gly His Thr Ser Ser Leu Val Arg Val Val Ser
                100                 105                 110
Thr Asn Tyr Asn Gln His Ala Met Val Phe Phe Lys Phe Val Phe Gln
                115                 120                 125
Asn Arg Glu Glu Phe Tyr Ile Thr Leu Tyr Gly Arg Thr Lys Glu Leu
                130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly
```

<210> SEQ ID NO 18
<211> LENGTH: 178
<212> TYPE: PRT
<213> ORGANISM: artificial
<220> FEATURE:
<223> OTHER INFORMATION: lipocalin mutein

<400> SEQUENCE: 18

```
Gln Asp Ser Thr Ser Asp Leu Ile Pro Ala Pro Pro Leu Ser Lys Val
1               5                   10                  15
Pro Leu Gln Gln Asn Phe Gln Asp Asn Gln Phe His Gly Lys Trp Tyr
                20                  25                  30
Val Val Gly Gln Ala Gly Asn Ile Arg Leu Arg Glu Asp Lys Asp Pro
            35                  40                  45
His Lys Met Met Ala Thr Ile Tyr Glu Leu Lys Glu Asp Lys Ser Tyr
        50                  55                  60
Asp Val Thr Gly Val Thr Phe Asp Lys Lys Cys Thr Tyr Ala Ile
```

```
                65                  70                  75                  80
Ser Thr Phe Val Pro Gly Ser Gln Pro Gly Glu Phe Thr Leu Gly Lys
                    85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
                115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 19
<211> LENGTH: 178
<212> TYPE: PRT
<213> ORGANISM: artificial
<220> FEATURE:
<223> OTHER INFORMATION: lipocalin mutein

<400> SEQUENCE: 19

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Lys Leu Arg Glu Asp Lys Asp Pro
            35                  40                  45

Asn Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Thr Tyr Ala Ile
65                  70                  75                  80

Ser Thr Leu Val Pro Gly Ser Gln Pro Gly Glu Phe Thr Phe Gly Lys
                    85                  90                  95

Ile Lys Ser Phe Pro Gly His Thr Ser Ser Leu Val Arg Val Val Ser
                100                 105                 110

Thr Asn Tyr Asn Gln His Ala Met Val Phe Phe Lys Phe Val Phe Gln
                115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 20
<211> LENGTH: 178
<212> TYPE: PRT
<213> ORGANISM: artificial
<220> FEATURE:
<223> OTHER INFORMATION: lipocalin mutein

<400> SEQUENCE: 20

Gln Asp Ser Thr Ser Asp Leu Ile Pro Ala Pro Pro Leu Ser Lys Val
1               5                   10                  15
```

```
Pro Leu Gln Gln Asn Phe Gln Asp Asn Gln Phe His Gly Lys Trp Tyr
            20                  25                  30
Val Val Gly Gln Ala Gly Asn Ile Arg Leu Arg Glu Asp Lys Asp Pro
        35                  40                  45
Ser Lys Met Met Ala Thr Ile Tyr Glu Leu Lys Glu Asp Lys Ser Tyr
 50                  55                  60
Asp Val Thr Ala Val Thr Phe Asp Asp Lys Lys Cys Asn Tyr Ala Ile
 65                  70                  75                  80
Ser Thr Phe Val Pro Gly Ser Gln Pro Gly Glu Phe Thr Leu Gly Lys
                85                  90                  95
Ile Lys Ser Phe Pro Gly His Thr Ser Ser Leu Val Arg Val Val Ser
            100                 105                 110
Thr Asn Tyr Asn Gln His Ala Met Val Phe Phe Lys Phe Val Phe Gln
        115                 120                 125
Asn Arg Glu Glu Phe Tyr Ile Thr Leu Tyr Gly Arg Thr Lys Glu Leu
130                 135                 140
Thr Ser Glu Leu Lys Glu Asn Phe Ile Arg Phe Ser Lys Ser Leu Gly
145                 150                 155                 160
Leu Pro Glu Asn His Ile Val Phe Pro Val Pro Ile Asp Gln Cys Ile
                165                 170                 175
Asp Gly

<210> SEQ ID NO 21
<211> LENGTH: 10
<212> TYPE: PRT
<213> ORGANISM: artificial
<220> FEATURE:
<223> OTHER INFORMATION: C-terminal tag 1

<400> SEQUENCE: 21

Ser Ala Trp Ser His Pro Gln Phe Glu Lys
1               5                   10

<210> SEQ ID NO 22
<211> LENGTH: 11
<212> TYPE: PRT
<213> ORGANISM: artificial
<220> FEATURE:
<223> OTHER INFORMATION: C-terminal tag 2

<400> SEQUENCE: 22

Pro Ser Ala Trp Ser His Pro Gln Phe Glu Lys
1               5                   10

<210> SEQ ID NO 23
<211> LENGTH: 8
<212> TYPE: PRT
<213> ORGANISM: artificial
<220> FEATURE:
<223> OTHER INFORMATION: Strep-tag

<400> SEQUENCE: 23

Trp Ser His Pro Gln Phe Glu Lys
1               5

<210> SEQ ID NO 24
<211> LENGTH: 456
<212> TYPE: DNA
<213> ORGANISM: artificial
<220> FEATURE:
<223> OTHER INFORMATION: lipocalin mutein
```

<400> SEQUENCE: 24

```
gcctcagacg aggagattca ggatgtgtca gggacgtggt atctgaaggc catgacggtg     60
gatgaggggt gtcgtccttg aatatatttt tcagttacgc caatgactct gactacccttt  120
gaaggcggca atctggaggc taaggtcacc atggcaatag atgggccggc acaggaggtg   180
aaagcagtgt tagagaagac agatgaaccg ggtaaatata cggccgatgg cggtaaacat   240
gttgcctata tcattcgcag ccatgtgaaa gatcattaca tcttttatag cgagggcgtg   300
tgcgatgggt ctcctgttcc aggggtgtgg ctcgtgggca gagaccccaa gaacaacctg   360
gaagccttgg aggactttga gaaagccgca ggagcccgcg gactcagcac ggagagcatc   420
ctcatcccca ggcagagcga aaccagctct ccaggg                              456
```

<210> SEQ ID NO 25
<211> LENGTH: 459
<212> TYPE: DNA
<213> ORGANISM: artificial
<220> FEATURE:
<223> OTHER INFORMATION: lipocalin mutein

<400> SEQUENCE: 25

```
acctcagacg aggagattca ggatgtgtca gggacgtggt atctgaaggc gatgacggtg     60
gatgagggt gtcgtccttg aatatatttt tcagttacgc caatgactct gactacccttt   120
gaaggcggca atctggaggc taaggtcacc atggcaatag atgggccggc acaggaggtg   180
agagcagtgt tagagaagac agatgaaccg ggtaaatata cggccgacgg cggtaaacat   240
gatgcctata tcattcgcag ccatgtgaaa gatcattaca tcttttatag cgagggcgtg   300
tgcgatgggt ctcctgttcc ggggtgtgg ctcgtgggca gagaccccga gaacaacctg    360
gaagccttgg aggactttga gaaaaccgca ggagcccgcg gactcagcac ggagagcatc   420
ctcatcccca ggcagagcga aaccagctct ccagggcca                           459
```

<210> SEQ ID NO 26
<211> LENGTH: 456
<212> TYPE: DNA
<213> ORGANISM: artificial
<220> FEATURE:
<223> OTHER INFORMATION: lipocalin mutein

<400> SEQUENCE: 26

```
gcctcagacg aggagattca ggatgtgtca gggacgtggt atctgaaggc gatgacggtg     60
gatgagggt gtcgtccttg aatatatttt tcagttacgc caatgactct gactacccttt   120
gaaggcggca atctggaggc taaggtcacc atggcaatag atgggccggc acaggaggtg   180
aacgcagtgt tagagaagac agatgaaccg ggtaaatata cggccgatgg cggtaaacat   240
gttgcctata tcattcgcag ccatgtgaga gatcattaca tcttttatag cgagggcgtg   300
tgcgatgggt ctcctgttcc ggggtgtgg ctcgtgggca gggaccccga gaacaacctg    360
gaagccttgg aggactttga gaaaaccgca ggagcccgcg gactcagcac ggagagcatt   420
ctcattccca ggcagagcga aaccagctct ccaggg                              456
```

<210> SEQ ID NO 27
<211> LENGTH: 459
<212> TYPE: DNA
<213> ORGANISM: artificial
<220> FEATURE:
<223> OTHER INFORMATION: lipocalin mutein

<400> SEQUENCE: 27

```
gtctcagacg aggagattca ggatgtgtca gggacgtggt atctgaaggc gatgacggtg      60
gatgagggt gtcgtccttg aatatatttt tcagttacgc caatgactct gactacccttt     120
gaaggcggca atctggaggc taaggtcacc atggcaatag atgggccggc acaggaggtg    180
agagcagtgt tagagaagac agatgaaccg ggtaaatata cggccgatgg cggtaaacat    240
gttgcctata tcattcgcag ccatgtgaaa gatcattaca tctttttatag cgagggcgtg    300
tgcgatgggt ctcctgttcc ggggtgtgg ctcgtgggca gacccccga aacaacctg      360
gaagccttgg aggactttga aaaaccgcga ggagcccgcg gactcagcac ggagagcatc    420
ctcatcccca ggcagagcga aaccagctct ccagggcca                           459
```

<210> SEQ ID NO 28
<211> LENGTH: 459
<212> TYPE: DNA
<213> ORGANISM: artificial
<220> FEATURE:
<223> OTHER INFORMATION: lipocalin mutein

<400> SEQUENCE: 28

```
gcctcagacg aggagattca ggatgtgtca gggacgtggt atctgaaggc gatgacggtg    60
gatgagggt gtcgtccttg aatatatttt tcagttacgc caatgactct gtctaccctt    120
gaaggcggca atctggaggc taaggtcacc atggcaatag atgggccggc acaggaggtg   180
aaagcagtgt tagagaagac agatgaaccg ggtaaatata cggccgatgg cggtaaacat   240
gttgcctata tcattcgcag ccatgtgaaa gatcattaca tctttttatag cgagggcgtg   300
tgcgatgggt ctcctgttcc ggggtgtgg ctcgtgggca gacccccaa gaacaacctg     360
gaagccttgg aggactttga aaagccgcga ggagcccgcg gactcagcac ggagagcatc   420
ctcatccca ggcagatcga aaccagctct ccagggcca                            459
```

<210> SEQ ID NO 29
<211> LENGTH: 459
<212> TYPE: DNA
<213> ORGANISM: artificial
<220> FEATURE:
<223> OTHER INFORMATION: lipocalin mutein

<400> SEQUENCE: 29

```
gcctcagacg aggagattca ggatgtgtca gggacgtggt atctgaaggc gatgacggtg    60
gatgagggt gtcgtccttg aatatatttt tcagttacgc caatgactct gactacccttt   120
gaaggcggca atctggaggc tgaggtcacc atggcaatag atgggccggc acaggaggtg   180
aaagcagtgt tagagaaggc agatgaaccg ggtaaatata cggccgatgg cggtaaacat   240
gttgcctata tcattcgcag ccatgtgaaa gatcattaca tctttttatag cgagggcgtg   300
tgcgatgggt ctcctgttcc ggggtgtgg ctcgtgggca gacccccaa gaacaacctg     360
gaagccttgg aggactttga aaaaccgcga ggagcccgcg gactcagcac ggagagcatc   420
ctcatccca gtcagatcga aaccagctct ccagggcca                            459
```

<210> SEQ ID NO 30
<211> LENGTH: 459
<212> TYPE: DNA
<213> ORGANISM: artificial
<220> FEATURE:
<223> OTHER INFORMATION: lipocalin mutein

<400> SEQUENCE: 30

```
acctcagacg aggagattca ggatgtgtca gggacgtggt atctgaaggc gatgacggtg    60
gatgaggggt gtcgtccttg gaatatattt tcagttacgc caatgactct gactacccett   120 gaagacggca atctggaggc taaggtcacc atggcaatag atgggccggc acaggaggtg   180
aaagcagtgt tagagaaggc agatgaaccg ggtaaatata cggccgatgg cggtaaacat   240
gttgcctata tcattcgcag ccatgtgaaa gatcattaca tcttttatag cgagggcgtg   300
tgcgatgggc tcctgttcc gggggtgtgg ctcgtgggca gagacccaa gaacaacctg    360 gaagccttgg aggactttga aaagccgca ggagcccgcg gactcagcac ggagagcatc    420
ctcatcccca ggcagatcga aaccagctct ccagggcca                          459
```

```
<210> SEQ ID NO 31
<211> LENGTH: 534
<212> TYPE: DNA
<213> ORGANISM: artificial
<220> FEATURE:
<223> OTHER INFORMATION: lipocalin mutein

<400> SEQUENCE: 31
caggactcca cctcagacct gatcccagcc ccacctctga gcaaggtccc tctgcagcag    60
aacttccagg acaaccaatt ccatgggaag tggtatgtgg taggtcaggc agggaatatc   120
aaactcagag aagacaaaga cccgaacaag atgatggcca ccatctatga gctgaaagaa   180
gacaagagct acaatgtcac cggtgtcact tttgacgaca agaagtgtac ttacgctatc   240 tctactttg ttccaggttc ccagccaggc gagttcacgc tggcaaaat taagagtttc     300 cctggacata cgagttctct cgtccgagtg gtgagcacca actacaacca gcatgctatg   360
gtgttcttca gttcgtttt ccaaaacagg gaggaattct acatcaccct ctacgggaga    420
accaaggagc tgacttcgga actaaaggag aacttcatcc gcttctccaa atctctgggc   480
ctccctgaaa accacatcgt cttccctgtc ccaatcgacc agtgtatcga cggc          534
```

```
<210> SEQ ID NO 32
<211> LENGTH: 534
<212> TYPE: DNA
<213> ORGANISM: artificial
<220> FEATURE:
<223> OTHER INFORMATION: lipocalin mutein

<400> SEQUENCE: 32
caggactcca cctcagacct gatcccagcc ccacctctga gcaaggtccc tctgcagcag    60
aacttccagg acaaccaatt ccatgggaaa tggtacgttg tcgggcaggc cggaaatatt   120
aggctgcgtg aggataagga tccgattaaa atgatggcga ccatttacga gttgaaagaa   180
gataaatcat atgacgtcac catggtgaag tttgatgata gaaatgcat gtacgatatt    240 tggacctttg tgccggggag ccagccgggc gagtttactt taggcaagat taaaagtttt   300
ccgggccata tcatcgtt ggtccgcgtc gtgagcacca actacaacca gcatgccatg     360
gtgttcttca gtttgtgtt tcagaaccgc gaggagtttt atatcacact gtacgggcgc    420
acgaaagaac tgacaagcga gctgaaggaa aattttatcc gcttttccaa atctctgggc   480
ctccctgaaa accacatcgt cttccctgtc ccaatcgacc agtgtatcga cggc          534
```

```
<210> SEQ ID NO 33
<211> LENGTH: 534
<212> TYPE: DNA
<213> ORGANISM: artificial
<220> FEATURE:
```

<223> OTHER INFORMATION: lipocalin mutein

<400> SEQUENCE: 33

```
caggactcca cctcagacct gatcccagcc ccacctctga gcaaggtccc tctgcagcag      60
aacttccagg acaaccaatt ccatgggaaa tggtacgttg tcgggcaggc cggaaatatt     120
aggctgcgtg aggataagga tccgaataaa atgatggcga ccatttacga gttgaaagaa     180
gataaatcat atgacgtcac cgcggtggcg tttgatgata agaaatgcac gtacgatatt     240
tggacctttg tgccggggag ccagccgggc gagtttactt taggcaagat taaaagtttt     300
ccgggccata catcatcgtt ggtccgcgtc gtgagcacca actacaacca gcatgccatg     360
gtgttcttca gtttgtgtt tcagaaccgc gaggagtttt atatcacact gtacgggcgc     420
acgaaagaac tgacaagcga gctgaaggaa aatttttatcc gcttttccaa atctctgggc     480
ctccctgaaa accacatcgt cttccctgtc ccaatcgacc agtgtatcga cggc            534
```

<210> SEQ ID NO 34
<211> LENGTH: 534
<212> TYPE: DNA
<213> ORGANISM: artificial
<220> FEATURE:
<223> OTHER INFORMATION: lipocalin mutein

<400> SEQUENCE: 34

```
caggactcca cctcagacct gatcccagcc ccacctctga gcaaggtccc tctgcagcag      60
aacttccagg acaaccaatt ccatgggaaa tggtacgttg tcgggcaggc cggaaatatt     120
aagctgcgtg aggataagga tccgaataaa atgatggcga ccatttacga gttgaaagaa     180
gataaatcat atgacgtcac cgcggtggcg tttgatgata agaaatgcac gtacgatatt     240
tggacctttg tgccggggag ccagccgggc gagtttactt taggcaagat taaaagtttt     300
ccgggccata catcatcttt ggtccgcgtc gtgagcacca actacaacca gcatgccatg     360
gtgttcttca gtttgtgtt tcagaaccgc gaggagtttt atatcacact gtacgggcgc     420
acgaaagaac tgacaagcga gctgaaggaa aatttttatcc gcttttccaa atctctgggc     480
ctccctgaaa accacatcgt cttccctgtc ccaatcgacc agtgtatcga cggc            534
```

<210> SEQ ID NO 35
<211> LENGTH: 525
<212> TYPE: DNA
<213> ORGANISM: artificial
<220> FEATURE:
<223> OTHER INFORMATION: lipocalin mutein

<400> SEQUENCE: 35

```
caggactcca cctcagacct gatcccagcc ccacctctga gcaaggtccc tctgcagcag      60
aacttccagg acaaccaatt ccatgggaaa tggtacgttg tcgggcaggc cggaaatatt     120
aagctgcgtg aggatagtaa aatgatggcg accatttacg agttgaaaga agataaatca     180
tatgacgtca ccggtgtgag ttttgatgat aagaaatgca cgtacgctat tatgaccttt     240
gtgccgggga gccagccggg cgagtttact ttaggcaaga ttaaaagttt tccgggccat     300
acatcatcgt tggtccgcgt cgtgagcacc aactacaacc agcatgccat ggtgttcttc     360
aagtttgtgt ttcagaaccg cgaggagttt tatatcacac tgtacgggcg cacgaaagaa     420
ctgacaagcg agctgaagga aaatttttatc cgcttttcca aatctctggg cctccctgaa     480
aaccacatcg tcttccctgt cccaatcgac cagtgtatcg acggc                      525
```

```
<210> SEQ ID NO 36
<211> LENGTH: 534
<212> TYPE: DNA
<213> ORGANISM: artificial
<220> FEATURE:
<223> OTHER INFORMATION: lipocalin mutein

<400> SEQUENCE: 36
caggactcca cctcagacct gatcccagcc ccacctctga gcaaggtccc tctgcagcag     60
aacttccagg acaaccaatt ccatgggaaa tggtacgttg tcgggcaggc cggaaatatt    120
aagctgcgtg aggataagga tccggttaaa atgatggcga ccatttacga gttgaaagaa    180
gataaatcat atgacgtcac cggggtgacg tttgatgata agaaatgcag gtacgatatt    240
tcgacctttg tgccggggag ccagccgggc gagtttactt ttggcaagat taaaagtttt    300
ccgggccata tcatcatcgt tggtccgcgt gtgagcacca actacaacca gcatgccatg    360
gtgttcttca gtttgtgtt tcagaaccgc gaggagtttt atatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534

<210> SEQ ID NO 37
<211> LENGTH: 534
<212> TYPE: DNA
<213> ORGANISM: artificial
<220> FEATURE:
<223> OTHER INFORMATION: lipocalin mutein

<400> SEQUENCE: 37
caggactcca cctcagacct gatcccagcc ccacctctga gcaaggtccc tctgcagcag     60
aacttccagg acaaccaatt ccatgggaaa tggtacgttg tcgggcaggc cggaaatatt    120
aggctgcgtg aggataagga tccgcataaa atgatggcga ccatttacga gttgaaagaa    180
gataaatcat atgacgtcac cggggtgact tttgatgata agaaatgcac gtacgctatt    240
tcgacctttg tgccggggag ccagccgggc gagtttactt taggcaagat taaaagtttt    300
ccgggccata tcatcatctt tggtccgcgt gtgagcacca actacaacca gcatgccatg    360
gtgttcttca gtttgtgtt tcagaaccgc gaggagtttt atatcacact gtacgggcgc    420
acgaaagaac tgacaagcga gctgaaggaa aattttatcc gcttttccaa atctctgggc    480
ctccctgaaa accacatcgt cttccctgtc ccaatcgacc agtgtatcga cggc          534

<210> SEQ ID NO 38
<211> LENGTH: 534
<212> TYPE: DNA
<213> ORGANISM: artificial
<220> FEATURE:
<223> OTHER INFORMATION: lipocalin mutein

<400> SEQUENCE: 38
caggactcca cctcagacct gatcccagcc ccacctctga gcaaggtccc tctgcagcag     60
aacttccagg acaaccaatt ccatgggaaa tggtacgttg tcgggcaggc cggaaatatt    120
aagctgcgtg aggataagga tccgaataaa atgatggcga ccatttacga gttgaaagaa    180
gataaatcat atgacgtcac cggggtgact tttgatgata agaaatgcac gtacgctatt    240
tctacccttg tgccggggag ccagccgggc gagtttactt ttggcaagat taaaagtttt    300
ccgggccata tcatcatcgt tggtccgcgt gtgagcacca actacaacca gcatgccatg    360
gtgttcttca gtttgtgtt tcagaaccgc gaggagtttt atatcacact gtacgggcgc    420
```

```
acgaaagaac tgacaagcga gctgaaggaa aattttatcc gcttttccaa atctctgggc      480
ctccctgaaa accacatcgt cttccctgtc ccaatcgacc agtgtatcga cggc            534
```

<210> SEQ ID NO 39
<211> LENGTH: 534
<212> TYPE: DNA
<213> ORGANISM: artificial
<220> FEATURE:
<223> OTHER INFORMATION: lipocalin mutein

<400> SEQUENCE: 39

```
caggactcca cctcagacct gatcccagcc ccacctctga gcaaggtccc tctgcagcag      60
aacttccagg acaaccaatt ccatgggaaa tggtacgttg tcgggcaggc cggaaatatt     120
aggctgcgtg aggataagga tccgtctaaa atgatggcga ccatttacga gttgaaagaa     180
gataaatcat atgacgtcac cgctgtgacg tttgatgata agaaatgcaa ttacgctatt     240
tctacctttg tgccggggag ccagccgggc gagtttactt taggcaagat taaaagtttt     300
ccgggccata catcatcgtt ggtccgcgtc gtgagcacca actacaacca gcatgccatg     360
gtgttcttca gtttgtgtt tcagaaccgc gaggagtttt atatcacact gtacgggcgc     420
acgaaagaac tgacaagcga gctgaaggaa aattttatcc gcttttccaa atctctgggc     480
ctccctgaaa accacatcgt cttccctgtc ccaatcgacc agtgtatcga cggc            534
```